United States Patent [19]

Murthy et al.

[11] Patent Number: 4,792,556
[45] Date of Patent: Dec. 20, 1988

[54] NAPHTHALENE ANTI-PSORIATIC AGENTS

[75] Inventors: D. V. K. Murthy, Cupertino; Michael C. Venuti, San Francisco; John M. Young, Redwood City, all of Calif.

[73] Assignee: Syntex (U.S.A.) Inc., Palo Alto, Calif.

[21] Appl. No.: 856,929

[22] Filed: Apr. 28, 1986

Related U.S. Application Data

[63] Continuation-in-part of Ser. No. 773,912, Sep. 9, 1985, abandoned.

[51] Int. Cl.<sup>4</sup> ............ A61K 31/22; A61K 31/275; A61K 31/415; A61K 31/44; C07C 69/35; C07C 121/15

[52] U.S. Cl. .................. 514/256; 514/269; 514/311; 514/312; 514/277; 514/344; 514/345; 514/398; 514/399; 514/406; 514/407; 514/419; 514/424; 514/427; 514/432; 514/461; 514/473; 514/510; 260/410.5; 260/408; 544/298; 544/318; 544/319; 546/153; 546/294; 546/301; 548/337; 548/346; 548/371; 548/372; 548/375; 548/484; 548/542; 548/543; 548/551; 548/556; 549/23; 549/28; 549/479; 560/8; 560/65; 560/73; 560/105; 560/108; 560/139

[58] Field of Search .............. 560/139, 8, 28, 65, 560/73, 105, 108; 514/510, 863, 269, 311, 312, 277, 344, 345, 398, 399, 406, 407, 419, 424, 427, 432, 461, 473; 260/410.5, 408; 558/413, 414; 544/298, 318, 319; 546/153, 294, 301; 548/337, 346, 371, 372, 375, 484, 542, 543, 551, 556; 549/23, 28, 479

[56] References Cited

U.S. PATENT DOCUMENTS 4,466,981 8/1984 Jones et al. .................. 548/337 X Primary Examiner—Michael L. Shippen Attorney, Agent, or Firm—Carol J. Roth; Tom M. Moran; Brian Lewis

[57] ABSTRACT

Psoriasis in mammals is relieved by topically administering naphthalenes of the formula:

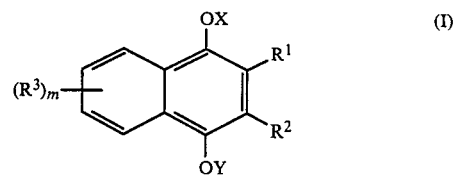

wherein:
$R^1$ and $R^2$ are the same and are lower alkoxy or optionally substituted phenoxy,
$R^3$ is lower alkyl, lower alkoxy, or halo and m is 0, 1 or 2 or $R^3$ is optionally substituted phenyl, optionally substituted phenyl lower alkyl, optionally substituted phenyl lower alkoxy, amino, lower alkylamino, lower dialkylamino, cyano, or $S(O)_n R$ wherein R is lower alkyl; optionally substituted phenyl; optionally substituted phenyl lower alkyl; or optionally substituted heterocyclic aryl of three to nine ring atoms containing one or two heteroatoms selected from the group consisting of nitrogen, oxygen and sulfur, and the pharmaceutically acceptable acid addition salts thereof; and m is 1 and n is 0, 1 or 2;
at least one of X or Y is C(O)W and the other X or Y is different and is hydrogen, C(O)W or $R^4$
wherein
W is alkyl of one to seven carbon atoms, optionally substituted phenyl or optionally substituted benzyl; and
$R^4$ is lower alkyl or optionally substituted phenyl-lower-alkyl.

18 Claims, No Drawings

NAPHTHALENE ANTI-PSORIATIC AGENTS

This is a continuation-in-part of U.S. Ser. No. 773,912 filed Sept. 9, 1985, now abandoned, which is incorporated herein in its entirety by reference.

BACKGROUND OF THE INVENTION

1. Field of the Invention

The invention relates to naphthalene derivatives which are useful in inhibiting certain dermatological conditions and inhibiting lipoxygenase activity, particularly 5-lipoxygenase activity which makes the compounds useful for topical treatment of inflammatory states. This invention also relates to pharmaceutical compositions useful in relieving the effects of certain chronic recurrent papulosquamous dermatoses, e.g., psoriasis. This invention also relates to a process for preparing compounds of this invention.

RELATED DISCLOSURES

Psoriasis is a skin disease characterized in part by excessive proliferation of cells of the epidermis which remain strongly adherent and build up into a scaley plaque typical of the disease. Currently available therapies, which are not curative, depend on the control of epidermal cell proliferation through the use of hormonal agents, such as corticosteroids or through the use of compounds related to cancer chemotherapy such as hydroxyurea, methotrexate, and the nitrogen mustards.

While the above agents are effective to a certain extent, they cause numerous severe undesirable side effects including renal irritation, hepatic toxicity, and erythema.

The compound, 2,3-dimethoxy-1,4-diacetyloxynaphthalene is known and is disclosed to be useful as a synthetic intermediate, but no useful biological activity has been described to it. See J. Chem. Res., Synop. 1980(4), 156–7 and An. Quim. 1976, 72(3): 247–53. Certain diester naphthalenes are known to be useful in treating psoriasis. See, for example, U.S. Pat. No. 4,466,981. Surprisingly, it has been discovered that the compounds of the instant invention are also effective antipsoriatic agents. Compounds of formula (Ib) and (Ic), infra, provide prolonged activity in the treatment of psoriasis because of their stability upon application and slow conversion to compounds of formula (Ia). Further, the compounds of the present invention are more stable in the topical formulations normally used.

SUMMARY

The present invention relates to a compound of the following formula

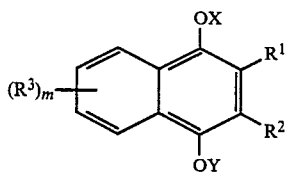

wherein:

$R^1$ and $R^2$ are the same and are lower alkoxy of one to six carbon atoms or phenoxy optionally substituted by one or two lower alkyl of one to four carbon atoms, lower alkoxy of one to four carbon atoms or halo;

$R^3$ is lower alkyl of one to six carbon atoms, lower alkoxy of one to six carbon atoms, or halo and m is 0, 1 or 2 or $R^3$ is optionally substituted phenyl, optionally substituted phenyl lower alkyl, optionally substituted phenyl lower alkoxy, amino, lower alkylamino, lower dialkylamino, halo, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and m is 1 and n is 0, 1 or 2;

at least one of X or Y is C(O)W and the other X or Y is different and is hydrogen, C(O)W or $R^4$ wherein W is alkyl of one to seven carbon atoms, phenyl or benzyl optionally substituted with one or two lower alkyl of one to four carbon atoms, lower alkoxy of one to four carbon atoms or halo; and $R^4$ is lower alkyl of one to six carbon atoms or phenyl-lower-alkyl of one to six carbon atoms wherein the phenyl ring is optionally substituted with one or two lower alkyl of one to four carbon atoms, lower alkoxy of one to four carbon atoms or halo.

Another aspect of the invention is a pharmaceutical composition in a form suitable for topical administration to mammals comprising a compound of formula (I) and a pharmaceutically acceptable excipient.

Another aspect of the invention is a method for relieving inflammatory diseases such as the condition of psoriasis in a mammal which comprises topically administering to said mammal a psoriasis-relieving amount of a compound of formula (I).

Yet another aspect of the invention is a novel process for preparing compounds of formula (I). Compounds of formula (1a) infra, which are intermediates for compounds of formula (1b) and (1c) infra, are prepared by carefully controlled hydrolysis of compound of formula (XII). Compounds of formula (1b) and (1c) are prepared by reacting compounds of formula (1a) with the appropriate reactant.

DETAILED DESCRIPTION AND PREFERRED EMBODIMENT

In its broadest aspect, the present invention relates to a compound of the following formula

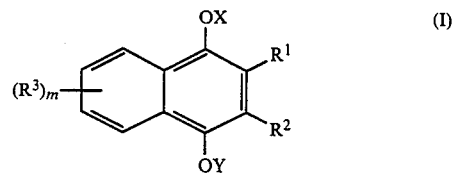

wherein:

$R^1$ and $R^2$ are the same and are lower alkoxy of one to six carbon atoms or phenoxy optionally substituted by one or two lower alkyl of one to four carbon atoms, lower alkoxy of one to four carbon atoms or halo;

$R^3$ is lower alkyl of one to six carbon atoms, lower alkoxy of one to six carbon atoms, or halo and m is 0, 1 or 2 or $R^3$ is optionally substituted phenyl, optionally substituted phenyl lower alkyl, optionally substituted phenyl lower alkoxy, amino, lower alkylamino, lower dialkylamino, halo, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and m is 1 and n is 0, 1 or 2; and at least one of X or Y is C(O)W and the other X or Y is different and is hydrogen, C(O)W or $R^4$ wherein W is alkyl of one to seven carbon atoms, phenyl or benzyl optionally substituted with one or two lower alkyl of one to four carbon atoms, lower alkoxy of one to four carbon atoms or halo; and $R^4$ is lower alkyl of one to four carbon atoms or phenyl-lower-alkyl of one to six carbon atoms wherein the phenyl ring is optionally substituted with one or two lower alkyl of one to four carbon atoms, lower alkoxy of one to four carbon atoms or halo.

The compounds of formula (I) may be divided into subgroups (Ia), (Ib) and (Ic).

Compounds of subgroup (Ia) are represented by formula (I) wherein either X or Y is hydrogen and the other is —C(O)W wherein $R^1$, $R^2$, $R^3$ and W are as defined above. Within this subgroup it is preferred that W is a sterically hindered group such as i-propyl, i-butyl, optionally substituted phenyl and 2,2-dimethylethyl with W being 2,2-dimethylethyl and optionally substituted phenyl being the most preferred.

Compounds of subgroup (Ib) are represented by formula (I) wherein X and Y are different and are —C(O)W and $R^1$, $R^2$, $R^3$ and W are as defined above. Within this subgroup is preferred that at least one W is a sterically hindered group such as i-propyl, i-butyl, optionally substituted phenyl and 2,2-dimethylethyl.

Compounds of subgroup (Ic) are represented by formula (I) wherein one X or Y is $R^4$ and the other is —C(O)W wherein $R^1$, $R^2$, $R^3$, $R^4$ and W are as defined above. Within this subgroup it is preferred that $R^4$ is lower alkyl of one to three carbon atoms such as methyl, ethyl, n-propyl and i-propyl.

An even more specific embodiment of the instant invention are compounds of formula (I) wherein m is 1 and $R^3$ is at the 6-position and is bromo, chloro, fluoro, cyano, methoxy, ethoxy, n-propoxy, i-propoxy, n-butoxy, and i-butoxy.

A preferred embodiment of the invention are compounds of formula (I) wherein m is 0.

Another embodiment of the invention are compounds wherein m is 2 and the two $R^3$s are at the 6 and 7 positions and are lower alkyl, lower alkoxy or halo with $R^3$ being methyl being preferred.

In the present specification and claims the term "alkyl" is intended to mean alkyl groups containing one to seven carbon atoms including straight chain groups, or branched chain groups. Illustrative of such groups are for example, methyl, ethyl, n-propyl, i-propyl, n-hexyl, 2-methylpentyl, n-heptyl, 2,2-dimethylbutyl and 3,3-dimethylpentyl. The term "lower alkyl" refers to alkyl groups of one to six carbon atoms as defined above. Examples of "lower alkyl" groups are methyl, ethyl, n-propyl, i-propyl, n-butyl, i-butyl, s-butyl, 2,2-dimethylpropyl and t-hexyl. The term "phenyl-lower-alkyl" refers to an optionally substituted phenyl ring attached to an alkylene chain of one to six carbon atoms.

The term "lower alkoxy" refers to a straight or branched chain aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy and n-pentyloxy. "Phenyl lower alkoxy" refers to a phenyl ring attached to an alkylene chain of one to six carbon atoms having bonded thereto an oxygen atom. Examples of "phenyl-lower-alkoxy" are benzyloxy, 4-chlorophenylethoxy and phenyl-n-propoxy.

The term "sterically hindered" refers to alkyl groups wherein branching occurs at the carbon adjacent to or one carbon removed from the carbonyl group or to optionally substituted phenyl.

Optionally substituted phenyl refers to a phenyl ring optionally substituted by one or more substituents selected from the group consisting of lower alkyl, lower alkoxy, halo, lower acyl, lower acyloxy, cyano, nitro, amino and lower acylamino unless otherwise defined.

The term "halo" refers to fluoro, chloro, and bromo. The term "cyano" refers to the group —CN. The term "amino" refers to the group —$NH_2$.

The term "lower alkylamino" refers to an amino group substituted by lower alkyl as is defined above. Examples of "lower alkylamino" are methylamino, ethylamino and n-butylamino.

The term "lower dialkylamino" refers to an amino group substituted by two lower alkyl groups. Examples of "lower dialkylamino" are di-n-methylamino, di-propylamino and methylethylamino.

The term "lower acyl" refers to the group $R^5C(O)$— wherein $R^5$ is a lower alkyl group of one to six carbon atoms or an optionally substituted phenyl group. Examples of "lower acyl" are acetyl, propanoyl, butanoyl and benzoyl. The term "lower alkoxycarbonylalkyl" refers to an ester group of the formula $R^6OC(O)$— substituted on an alkyl group wherein $R^6$ is lower alkyl as is defined above. Examples of "lower alkoxycarbonylalkyl" are methoxycarbonylmethyl, ethoxycarbonylmethyl, ethoxycarbonylethyl, n-propoxycarbonylethyl and the like.

The term "heterocyclic aryl" is defined as those cyclic aromatic compounds having 3 to 9 ring carbon atoms and having one or two heteroatoms in the ring selected from the group consisting of nitrogen, oxygen and sulfur. Examples of such include the groups thiapyranyl, benzothiapyranyl, furyl, pyrrolyl, imidazolyl, pyrazolyl, pyridinyl, pyrimidinyl, indolyl, quinolinyl, indazolyl and the like. These heterocyclic aryls may be optionally substituted with halo, lower alkyl, cyano and lower alkoxy.

By the term "pharmaceutically acceptable acid addition salts" as used in the case of the various $R^3$ containing heterocyclic aryl substituents herein is intended to mean those non-toxic pharmaceutically acceptable acid addition salts which do not adversely affect the pharmaceutical properties of the parent compounds. With respect to these addition salts, suitable inorganic anions include, for example, chloride, bromide, iodide, sulfate, phosphate, nitrate, and the like. Suitable organic anions include, for example, acetate, benzoate, lactate, picrate, propionate, butyrate, valerate, tartrate, maleate, fumarate, citrate, succinate, tosylate, ascorbate, nicotinate, adipate, gluconate and the like.

The compounds of formula (I) wherein $R^3$ is other than hydrogen and m is 1 or 2 exist as regioisomers (position isomers). The isomers may be separated at any stage of the preparation of Ib or Ic from Ia, but it is preferred to separate the isomeric mixture of compounds of formula (Ia), i.e., compounds wherein there is a hydroxy group in the 1 or 4 position. The individual isomers of compounds of formula (Ib) or (Ic) may then be prepared. The isomers may be separated by crystallization, normal or reverse phase HPLC or other partition chromatographic techniques, and the like.

The claims and specification of this patent application are intended to encompass each individual isomer of formula (I) alone or in combination with its regioisomer, unless specifically designated otherwise.

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthalenes of formula (I) may be formulated with suitable pharmaceutical vehicles known in the art to form particularly effective topical compositions. An effective amount of the naphthalene compound is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture (15% or more glycol) | 50-99 parts by weight |
| Fatty Alcohol | 1-20 |
| Non-ionic Surfactant | 0-10 |
| Mineral Oil | 0-10 |
| Typical Pharmaceutical Adjuvants | 0-5 |
| Active Ingredients | 0.001-10 |

The fatty alcohol, non-ionic surfactant, and other adjuvants are discussed in U.S. Pat. No. 3,934,013 to Poulsen which is incorporated herein by reference.

The naphthalenes of formula (I) may also be formulated as topical ointments. A "classical" ointment is a semisolid anhydrous composition which may contain mineral oil, white petrolactum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White Petrolatum | 40-94 parts by weight |
| Mineral Oil | 5-20 |
| Glycol Solvent | 1-15 |
| Surfactant | 0-10 |
| Stabilizer | 0-10 |
| Active Ingredients | 0.001-10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Oct. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | |
|---|---|
| Active Ingredients | 0.001-10.0 parts by weight |
| Propylene Carbonate | 1-10 |
| Solvent | 1-10 |
| Surfactant | 0-10 |
| White Petrolatum | 70-97 |

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

| | |
|---|---|
| Gylcol Solvent | 40-35 parts by weight |
| Fatty Alcohol | 15-45 |
| Compatible Plasticizer | 0-15 |
| Compatible Coupling Agent | 0-15 |
| Penetrant | 0-20 |
| Active Ingredients | 0.001-10.0 |

Another aspect of the invention is a method for relieving the condition of psoriasis in a mammal by topically administering a composition containing a compound of formula (I) wherein n, $R^1$, $R^2$, $R^3$, $R^4$, W, X, Y, m and n are as defined above. Generally, the antipsoriatic manifestation in mammals, particularly humans, is combatted by contacting the inflamed areas with a therapeutically effective amount of the naphthalene-containing compositions of this invention, that is, an amount which results in a lessening of the epidermal cell proliferation (an anti-psoriatic effect). Preferably the naphthalenes are first formulated to prepare a suitable pharmaceutical formulation, as discussed hereinabove, which is then placed in contact with the afflicted area(s). An effective amount of the naphthalene compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an antipsoriatic response, but not enough to adversely effect the recipient, is applied to the afflicted area(s).

The compounds of this invention are also useful for treating mammals having a variety of disease states caused by lipoxygenase activity, particularly 5-lipoxygenase activity.

In vitro lipoxygenase inhibiting activity of the compounds of this invention are determined by the standard Human Polymorphonuclear Leukocytes assay. This assay is a modification of that described by O. Radmark, C. Malmsten, and B. Samuelsson in *FEBS Letter,* 110, 213–215, 1980. In vivo lipoxygenase inhibiting activity of the compounds of this invention are determined by the arachidonic acid mouse ear inflammation assay as described by J. M. Young, D. A. Spires, C. J. Bedord, B. Wagner, S. J. Ballaron and L. M. DeYoung in *Journal of Investigative Dermatology,* 82, 367–371, 1984.

PREPARATION

The compounds of formula (I) may be prepared from compounds of formula (XII) which may be prepared from compounds of formula (V) or (VI).

The intermediates of formula (V) or (VI) wherein m is 1 may be prepared by the Reaction Sequence below.

Reaction Sequence I

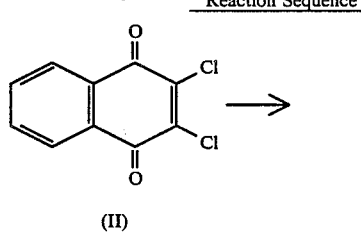

(II)

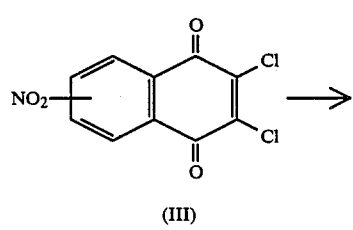

(III)

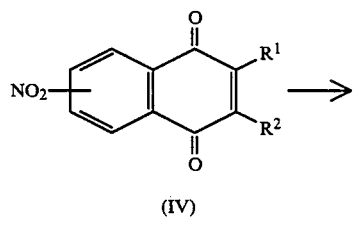

(IV)

-continued
Reaction Sequence I

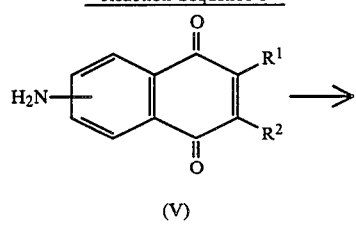

(V)

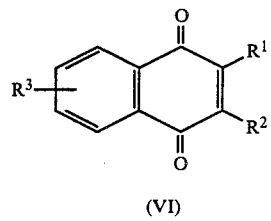

(VI)

wherein $R^1$, $R^2$, $R^3$ are as defined above and m is 1.

Compounds of formula (III) are prepared by starting with a 2,3-dihalonaphthoquinone, preferably 2,3-dichloro-1,4-naphthoquinone (compound of formula (II)), which is available from, i.a., Aldrich Chemical Co., and directly nitrating. The reaction proceeds in the manner known for polycyclic aromatic compounds to yield a mixture of the 5- and 6-nitro-2,3-dichloro-1,4-naphthoquinones, compounds of formula (III). The reaction is conducted typically with concentrated nitric acid in a low pH solvent medium, preferably concentrated sulfuric acid, typically at 20° C. to 100° C. for a time sufficient to complete the reaction. Depending on the reaction temperature and times of reaction, ratios of the 5-nitro isomer:6-nitro isomer mixture may range from 10:1 to 1:10, typically 8:1.

Compounds of formula (IV) are synthesized from 5- and 6-nitro-2,3-dichloro-1,4-naphthoquinone, compound of formula (III), by condensing them with an alkali metal alkoxide or phenoxide, wherein the alkoxy or phenoxy moiety is $R^1=R^2$. The reaction is preferably conducted in an inert organic solvent such as tetrahydrofuran, dimethylsulfoxide, dimethylformamide and the like at temperatures from about 20° C. to about 100° C. for a time sufficient to assure completeness of reaction, i.e., for about 2 hours to about 48 hours.

The compounds of formula (V) are prepared from compounds of formula (IV) by catalytic or non-catalytic reduction processes known in the prior art. Metal-acid reducing agent compositions, such as granulated iron and hydrochloric acid, tin and hydrochloric acid, and the like or neutral reducing agent compositions such as zinc dust and aqueous alcohol or aluminum amalgam and aqueous alcohol as well as organo-metallic reducing agents such as lithium aluminum hydride, sodium borohydride and the like may be used in this reduction. Preferably, the reduction is accomplished by treating the compounds of formula (IV) with excess hydrazine in the presence of a catalytically sufficient amount of palladium, typically on carbon. The reaction readily occurs at room temperature, the time of reaction being governed by the rate of addition of the hydrazine to the reaction mixture such typically being about 1 to about 10 hours.

Compounds of formula (VI) wherein $R^3$ is hydrogen may be prepared by reacting compound of formula (II)

with an alkali metal alkoxide or phenoxide as described hereinabove.

Compounds of formula (VI) wherein $R^3$ is lower alkylamino or lower dialkylamino are prepared by reacting compounds of formula (V) with an alkyl halide such as methyl iodide by methods well known in the art for alkylating amino groups. The following compounds, for example, may be prepared:
6-methylamino-2,3-dimethoxy-1,4-naphthoquinone;
6-diethylamino-2,3-dimethoxy-1,4-naphthoquinone; and
6-ethylamino-2,3-dimethoxy-1,4-naphthoquinone.

Compounds of formula (V) are converted into compounds of formula (VI) where $R^3$ is halo by adding to the compound of formula (V) in an acidified aqueous solution, a solution of an alkali metal nitrite. This initial reaction forms the diazonium salt at the 5- or 6-position of the naphthoquinone ring. The salt is decomposed with a solution of cuprous halide dispersed or dissolved in the corresponding halogen acid (the Sandmeyer reaction). This classical reaction is treated extensively in Bigelow, Org. Synthesis, Coll. Vol. I, 126–133 (1941).

A modification of the above Sandmeyer reaction is useful in the preparation of the compounds of formula (VI) where $R^3$ is cyano in that the diazonium salt, rather than being decomposed in the presence of cuprous halide/halogen acid is decomposed in the presence of an alkali metal cyanide and a cuprous halide. See Clarke and Read, Org. Synthesis, Coll. Vol. I, 514 (1941) for a further explanation of the considerations involved in this modified Sandmeyer reaction.

The compounds of formula (VI) where $R^3$ is an optionally substituted heterocyclic arylthio group, optionally substituted phenylthio or alkylthio may also be prepared from the diazonium salt (above). For example, the diazonium salt of the compound of formula (V) is reacted with an alkali solution of thiophenol to yield the compounds of formula (VI) where $R^3$ is phenylthio. Typically, the displacement reaction of the diazonium salt is carried out at 30°–75° C. by adding an alkali solution of thiophenol in an inert organic solvent. Solvents of preference are the inert solvents such as ethyl acetate, tetrahydrofuran and the like. Reaction times may vary from 10 minutes to about 24 hours.

The heterocyclic arylthio compounds are preferably prepared by adding the or 6-nitro-1,4-naphthoquinone compound of formula (IV) to a solution of the thiol-substituted heterocyclic aryl compound admixed with an alkali metal hydride in an inert organic solvent such as dimethylformamide. The reaction is typically conducted at −75° to −25° C. over a period of about 10 to about 60 minutes.

The preferred procedure for the preparation of the compounds of formula (VI) where $R^3$ is a linear or branched alkylthio or an optionally substituted phenylalkylthio is by first converting a compound of formula (V) to the di(2,3-$R^1$,$R^2$-1,4-naphthoquinone)-5 or 6-disulfide of the following formula:

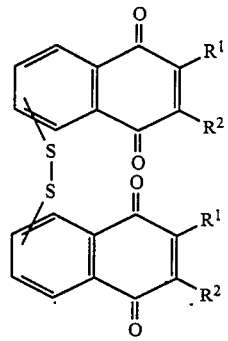

(VII)

wherein $R^1$ and $R^2$ are as defined above. A mixture of an alkaline earth or alkali metal thiol carboxylate such as the acetate, propanoate, butanoate and the like (compounds of the formula

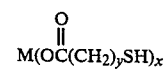

where y is the integer 0 to 18, M is an alkali or alkaline earth metal and x is the valence of said metal) in an inert organic solvent is added to a solution or dispersion of compound of formula (V) at a temperature of −10° to +10° C. over a period of about 1 to about 120 minutes, preferably 5 to 30 minutes. Reaction media include a variety of polar inert solvents such as dimethylformamide, dimethylsulfoxide and the like. After further reaction, typically for about 1 to about 10 hours at 20° to 50° C., the disulfide is isolated. This compound can then be used to prepare the alkyl or phenylalkyl sulfides of formula (VI) by first treating the disulfide with sodium borohydride in an inert organic solvent and adding to such mixture at a temperature of about −10° C. to about 75° C. for 1 to 10 hours an appropriate alkylating agent such as a dialkyl sulfate, an alkyl halide, an phenylalkyl halide and the like. Illustrative of such alkylating agents are the compounds methyl bromide, methyl iodide, dimethyl sulfate and benzyl bromide. Preferably alkyl iodide is used as the alkylating agent herein.

Where appropriate, salts of the compounds bearing heterocyclic aryl substituents are prepared. For example, the methylsulfate salt of the 2,3-dialkoxy-5-(pyridin-4-ylthio)-1,4-naphthoquinone is readily prepared by admixture with dimethylsulfate in an inert organic solvent such as tetrahydrofuran. Salt formations of this type are well known in the prior art.

A particularly preferred method of preparing compounds of formula (VI) wherein $R^3$ is 6-halo is shown in the following reaction sequence.

REACTION SEQUENCE II

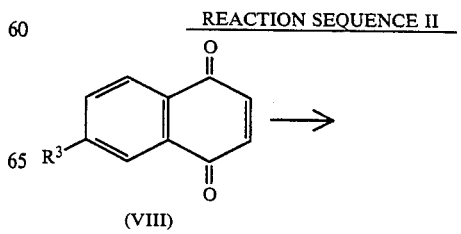

(VIII)

REACTION SEQUENCE II -continued

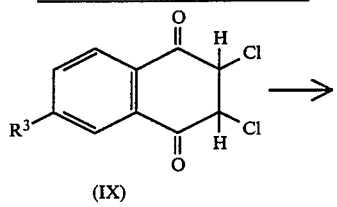

(IX)

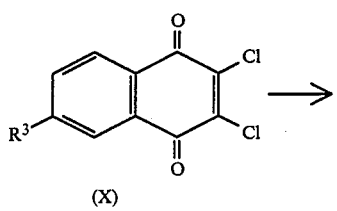

(X)

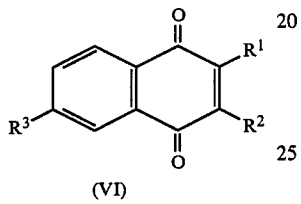

(VI)

wherein R¹ and R² are as defined above and m is 1.

Compounds of formula (VIII) are prepared according to the method disclosed in J. Am. Chem. Soc., 70, 3165 (1948) and Ibid., 71, 3615 (1949). Halo substituted 1,3-butadiene is reacted with 1,4-benzoquinone in a solvent such as acetic acid at a temperature of −10° C. to 30° C., preferably at 25° C. for 24 to 72 hours, preferably from 40 to 48 hours. The 5,7-dihydro compound which is formed is recovered and treated with an oxidizing agent such as sodium dichromate, sodium nitrite and the like as described in the above articles to form compounds of formula (VIII). Compounds of formula (IX) are prepared by bubbling chlorine gas into a solution of compound of formula (VIII) in a solvent such as glacial acetic acid, nitrobenzene, carbon tetrachloride and the like, preferably glacial acetic acid at room temperature. This compound, which may be isolated by known means, dissolved in a solvent such as acetic acid is treated with chlorine gas and a suitable catalyst such as sodium acetate, iodine, iron(III)chloride, dimethylformamide or alcohols with heating under reflux for ½ to 4 hours, preferably for 1 to 2½ hours to yield compounds of formula (X). Compounds of formula (VI) wherein R³ is halo are prepared by reacting compound of formula (X) with an alkali metal alkoxide or phenoxide such as sodium alkoxide or phenoxide, e.g., sodium methoxide or sodium phenoxide in an anhydrous solvent such as methanol, dimethylformamide and the like, the solvent being chosen according to the length of the alkyl chain on the alkoxy group. The reaction mixture is heated under reflux for ½ to 3 hours, preferably for ½ to 1½ hours. Compounds of formula (VI) are recovered by conventional means such as by crystallization.

The intermediate, 2-chloro-1,3-butadiene (chloroprene) is available from, i.a., Pfaltz and Bauer Chemical Co. 2-Bromo-1,3-butadiene and 2-fluoro-1,3-butadiene may be prepared by methods well known in the art, for example, by the methods discussed in J. Am. Chem. Soc., 55 786 (1933) and U.S. Pat. No. 2,401,850, respectively.

The intermediates of formula (VI) wherein R³ is lower alkyl, lower alkoxy, optionally substituted phenyl, optionally substituted phenyl lower alkyl or optionally substituted phenyl lower alkoxy may be prepared by methods well known in the art such as by reacting the diazonium salt of compound of formula (V) with an appropriate compound such as an alcohol e.g. methanol, ethanol, benzyl alcohol and the like. These intermediates may also be prepared by the method set out in Reaction Sequence (II) wherein the 2-halo-1,3-butadiene is replaced by the appropriate 1,3-butadiene such as 2-methyl-1,3-butadiene(isoprene), 2-ethyl-1,3-butadiene, 2,3-dimethyl-1,3-butadiene and the like.

Compounds of formula (XII) which are converted to compounds of formula (Ia) are prepared from compounds of formula (VI) by the Reaction Sequence shown below.

REACTION SEQUENCE III

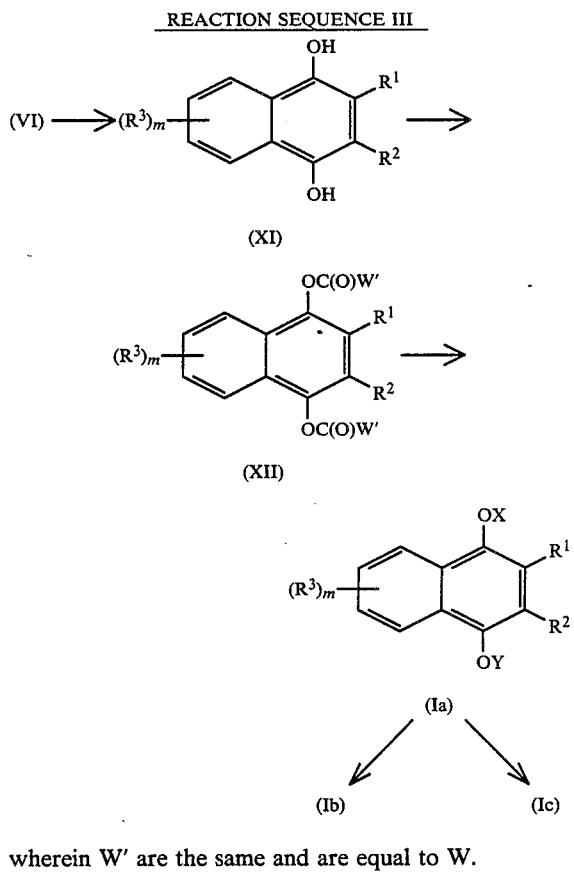

wherein W' are the same and are equal to W.

Compounds of formula (XII) are prepared from compounds of formula (VI) by first hydrogenating to form compounds of formula (XI) in a hydrogen atmosphere in the presence of a catalyst such as palladium on charcoal and then reacting the hydrogenated compound with an acylating agent such as an appropriate anhydride and pyridine such as acetic anhydride, benzoic acid anhydride and the like in a solvent such as tetrahydrofuran, diethyl ether and the like. Acyl halides may also be used to acylate compounds of formula (XII) but acyl anhydrides are preferred. Compounds of formula (XII) are recovered by crystallization.

The acid anhydrides are commercially available from, i.a., Aldrich Chemical Co. or if not available may be prepared by condensing the appropriate acid in the presence of acetic anhydride or acetyl chloride containing a trace of phosphoric acid. The anhydride is recovered by distillation or crystallization.

The sulfinylnaphthalenes of formula (XII) are prepared by oxidation of the corresponding thio compounds with a stoichiometric amount of a suitable peracid in an inert organic solvent.

The compounds of formula (XII) bearing a sulfonyl substituent are prepared by further oxidizing the compounds of formula (XII) wherein $R^3$ is a sulfinyl group with a suitable peracid typically at $-10°$ to $75°$ C. for 1 to 10 hours. Preferably, m-chloroperbenzoic acid in an inert organic solvent at room temperature is used to prepare the desired sulfonyl compounds.

The compounds of formula (Ia), i.e., compounds wherein either X or Y is hydrogen, are prepared by a novel hydrolysis process wherein the pH of the reaction mixture is carefully controlled and maintained at pH 7.5 to 9.5 preferably pH 8–9. If general hydrolysis conditions are employed both ester groups are removed from the compound of formula (XII) to form compound of formula (XI) which will eventually revert to the 1,4-naphthoquinone.

Compound of formula (XII), dissolved in a mixture consisting of a pH 8–9 buffer solution such as a phosphate buffer solution and the like, and a solvent such as acetonitrile, dimethylformamide and the like, is heated to 40° C. to 120° C., preferably to 50° C. to 100° C. for 1 to 15 days, preferably for 2 to 12 days. The reaction is monitored by, e.g., thin layer chromatography. Additional buffer is added, if necessary, to maintain pH 8–9. Compound of formula (Ia) is recovered by, e.g., extraction and purified by recrystallization. If compound of formula (Ia) exists as the isomeric mixture the mixture, if desired, is separated by preparative high pressure liquid chromatography using silica gel and eluting with anhydrous methanol/hexane, or other suitable solvents.

Compounds of formula (Ib) are prepared from compounds of formula (Ia) by reaction with an acylating agent such as an acyl halide or an acid anhydride such as acetic anhydride, 2,2-dimethylpropanoic acid anhydride, benzoic acid anhydride and the like, and pyridine/dimethylaminopyridine in a solvent such as tetrahydrofuran. Compounds of formula (Ib) are recovered by, e.g., recrystallization.

Compounds of formula (Ic) may be prepared by reacting a compound of formula (Ia) with an alkylating agent such as an alkyl tosylate, an alkyl mesylate or an alkyl or phenylalkyl halide such as benzyl bromide, i-propyl bromide, n-butyl bromide, phenylethyl bromide and the like.

To a solution of a compound of formula (Ia) and an alkylating agent such as an alkyl or arylalkyl halide in a solvent such as tetrahydrofuran, dimethylformamide and the like, is added an equivalent amount of an amine base such as 1,8-diazobicyclo-[5.4.0]undec-7-one (DBU). The solution at room temperature or heated to 120° C., preferably is maintained at room temperature or heated to 60° C. for ½ hour to five hours, preferably for 1 hour to 3 hours. Compound of formula (Ic) is recovered by, e.g., evaporation followed by chromatography.

Compounds of formula (Ic) may also be prepared by reacting compound of formula (Ia) with a diazoalkane such as diazomethane, diazoethane, diazophenylmethane and the like.

Compounds of formula (Ic) wherein either X or Y is methyl are preferably prepared by reacting compound of formula (Ia) with diazomethane.

A solution of compound of formula (Ia) in a solvent such as ether is treated with a solution of diazomethane in a solvent such as ether generated in situ from N-methyl-N-nitroso-p-toluenesulfonamide (Diazald®). The compound of formula (Ic) is recovered by evaporation followed by flash chromatograhy over silica gel.

DBU and Diazald® are available from, i.a., Aldrich Chemical Co. The alkyl and arylalkyl halides are readily available from, i.a., Aldrich Chemical Co. or may be made by methods well known in the art.

The following specific description is given to enable those skilled in the art to more clearly understand and practice the present invention. It should not be considered as a limitation upon the scope of the invention but merely as illustrative and representative thereof.

PREPARATION 1

2,3-Dichloro-5- and 6-nitro-1,4-naphthoquinone (Preparation of Compounds of Formula (III))

Finely powdered 2,3-dichloro-1,4-naphthoquinone 50 g. 0.22 mol) was added to a stirred mixture of concentrated sulfuric acid (170 ml) and 90% nitric acid (102 ml) at a rate so that the exothermic reaction raised the temperature to 60° C. The resulting mixture was stirred at 60° C. for a further 2 hours. The yellow crystalline solid was filtered off, washed thoroughly with water and recrystallized from chloroform giving 22.9 g of the 5-nitro isomer, mp 156°–157° C. The above strongly acidic filtrate was poured onto ice water. The resultant solid was filtered off, washed thoroughly with water and dried giving 20.8 g of a mixture of the 5- and 6-isomer. Fractional crystallization of this mixture from acetic acid and chloroform:isopropanol afforded 2.8 g of the 6-nitro isomer, mp 184°–187° C.

Further quantities of both 5- and 6-isomer were obtained from the recrystallization mother liquors by chromatography on a silica gel column eluting with chloroform:cyclohexane mixtures.

PREPARATION 2

2,3-Dimethoxy-5-nitro-1,4-naphthoquinone (Preparation of Compounds of Formula (IV))

A. A solution of 2,3-dichloro-5-nitro-1,4-naphthoquinone (2.72 g, 10 mmol) in anhydrous tetrahydrofuran (15 ml) was added to a solution of 1N sodium methoxide (25 ml, 25 mmol) and the resulting solution stored at 22° for 16 hours. Acetic acid (1 ml) was then added, the solution concentrated in vacuo and the residue partitioned between water (50 ml) and chloroform (100 ml). The aqueous phase was further extracted with chloroform (2×50 ml). The combined chloroform extracts were dried with MgSO$_4$ and concentrated in vacuo. The residue was recrystallized from methanol giving 1.99 g of 2,3-dimethoxy-5-nitro-1,4-naphthoquinone, mp 156°–157°.

B. Similarly, using the above procedure in Part A, substituting 2,3-dichloro-6-nitro-1,4-naphthoquinone, where appropriate, for 2,3-dichloro-5-nitro-1,4-naphthoquinone and the appropriate sodium alkoxide or sodium phenoxide for sodium methoxide, the following compounds are prepared:

2,3-dimethoxy-6-nitro-1,4-naphthoquinone, mp 113°–114° C.;
2,3-diethoxy-5-nitro-1,4-naphthoquinone;
2,3-diethoxy-6-nitro-1,4-naphthoquinone;
2,3-di-n-propoxy-5-nitro-1,4-naphthoquinone;

2,3-di-n-propoxy-6-nitro-1,4-naphthoquinone;
2,3-di-i-propoxy-5-nitro-1,4-naphthoquinone;
2,3-di-i-propoxy-6-nitro-1,4-naphthoquinone;
2,3-di-n-butoxy-5-nitro-1,4-naphthoquinone;
2,3-di-n-butoxy-6-nitro-1,4-naphthoquinone;
2,3-di-s-butoxy-5-nitro-1,4-naphthoquinone;
2,3-di-s-butoxy-6-nitro-1,4-naphthoquinone;
2,3-di-n-pentyloxy-5-nitro-1,4-naphthoquinone;
2,3-di-n-pentyloxy-6-nitro-1,4-naphthoquinone;
2,3-di-s-pentyloxy-5-nitro-1,4-naphthoquinone;
2,3-di-s-pentyloxy-6-nitro-1,4-naphthoquinone;
2,3-di-n-hexyloxy-5-nitro-1,4-naphthoquinone;
2,3-di-n-hexyloxy-6-nitro-1,4-naphthoquinone;
2,3-di-i-hexyloxy-5-nitro-1,4-naphthoquinone;
2,3-di-i-hexyloxy-6-nitro-1,4-naphthoquinone;
2,3-di(2,2-dimethylpropoxy)-5-nitro-1,4-naphthoquinone;
2,3-di(2,2-dimethylpropoxy)-6-nitro-1,4-naphthoquinone;
2,3-diphenoxy-6-nitro-1,4-naphthoquinone;
2,3-di(4-chlorophenoxy)-6-nitro-1,4-naphthoquinone;
2,3-diphenoxy-5-nitro-1,4-naphthoquinone;
2,3-di(4-methoxyphenoxy)-6-nitro-1,4-naphthoquinone;
2,3-di(2,4-dichlorophenoxy)-6-nitro-1,4-naphthoquinone; and
2,3-di(3-methylphenoxy)-6-nitro-1,4-naphthoquinone.

PREPARATION 3

2,3-Dimethoxy-5-amino-1,4-naphthoquinone (Preparation of Compounds of Formula (V))

Hydrazine (4.0 ml, 125 mmol of 97%) was added dropwise, over a 2 hour period, to a stirred mixture of the captioned compound of Preparation 2 (19.9 g, 75.6 mmol), 5% palladium on carbon (10 g) and ethanol (750 ml) in a nitrogen atmosphere. The catalyst was filtered off through a celite pad that was washed with hot ethanol (2×300 ml). The combined filtrate and washings were concentrated to dryness in vacuo and the residue recrystallized from water:ethanol (1.5:1) giving 14.6 g of 2,3-dimethoxy-5-amino-1,4-naphthoquinone, mp 116°–117°.

Similarly, substituting the compounds from Preparation 2 for 2,3-dimethoxy-5-nitro-1,4-naphthoquinone the following compounds are prepared:
2,3-dimethoxy-6-amino-1,4-naphthoquinone, mp 196°–197° C.;
2,3-diethoxy-5-amino-1,4-naphthoquinone;
2,3-diethoxy-6-amino-1,4-naphthoquinone;
2,3-di-n-propoxy-5-amino-1,4-naphthoquinone;
2,3-di-n-propoxy-6-amino-1,4-naphthoquinone;
2,3-di-i-propoxy-5-amino-1,4-naphthoquinone;
2,3-di-i-propoxy-6-amino-1,4-naphthoquinone;
2,3-di-n-butoxy-5-amino-1,4-naphthoquinone;
2,3-di-n-butoxy-6-amino-1,4-naphthoquinone;
2,3-di-s-butoxy-5-amino-1,4-naphthoquinone;
2,3-di-s-butoxy-6-amino-1,4-naphthoquinone;
2,3-di-n-pentyloxy-5-amino-1,4-naphthoquinone;
2,3-di-n-pentyloxy-6-amino-1,4-naphthoquinone;
2,3-di-s-pentyloxy-5-amino-1,4-naphthoquinone;
2,3-di-s-pentyloxy-6-amino-1,4-naphthoquinone;
2,3-di-n-hexyloxy-5-amino-1,4-naphthoquinone;
2,3-di-n-hexyloxy-6-amino-1,4-naphthoquinone;
2,3-di-i-hexyloxy-5-amino-1,4-naphthoquinone;
2,3-di-i-hexyloxy-6-amino-1,4-naphthoquinone;
2,3-di(2,2-dimethylpropoxy)-5-amino-1,4-naphthoquinone;
2,3-di(2,2-dimethylpropoxy)-6-amino-1,4-naphthoquinone;
2,3-diphenoxy-6-amino-1,4-naphthoquinone;
2,3-di(4-chlorophenoxy)-6-amino-1,4-naphthoquinone;
2,3-di(4-methoxyphenoxy)-6-amino-1,4-naphthoquinone;
2,3-di(2,4-dichlorophenoxy)-6-amino-1,4-naphthoquinone; and
2,3-di(3-methylphenoxy)-6-amino-1,4-naphthoquinone.

PREPARATION 4

5-Chloro-2,3-dimethoxy-1,4-naphthoquinone (Preparation of Compounds of Formula (VI) where $R^3$ is 5-chloro)

A solution of sodium nitrite (0.69 g, 10 mmol) in water (5 ml) was added at 0°–5° C. to a solution of 5-amino-2,3-dimethoxy-1,4-naphthoquinone (1.17 g, 5 mmol) in 5:1 acetic acid:water (25 ml) containing concentrated hydrochloric acid (1.7 ml). A further quantity of sodium nitrite (0.69 g) was then added to the reaction mixture after cooling to −5° C., followed by a solution of cuprous chloride (0.6 g) in concentrated hydrochloric acid (5 ml). The mixture was allowed to warm to 22° C. and solid cuprous chloride was added portionwise until the mixture assumed a green color. Water was then added to the reaction mixture and the precipitated yellow solid filtered off, washed with water and recrystallized from methanol:water (2:1) giving 1.01 g of 5-chloro-2,3-dimethoxy-1,4-naphthoquinone, mp 120°–121° C.

Similarly, proceeding as above substituting the appropriate compounds for 2,3-dimethoxy-5-amino-1,4-naphthoquinone the following compounds are prepared:
6-chloro-2,3-dimethoxy-1,4-naphthoquinone;
5-chloro-2,3-diethoxy-1,4-naphthoquinone;
6-chloro-2,3-diethoxy-1,4-naphthoquinone;
5-chloro-2,3-di-n-propoxy-1,4-naphthoquinone;
6-chloro-2,3-di-n-propoxy-1,4-naphthoquinone;
5-chloro-2,3-di-i-propoxy-1,4-naphthoquinone;
6-chloro-2,3-di-i-propoxy-1,4-naphthoquinone;
5-chloro-2,3-di-n-butoxy-1,4-naphthoquinone;
6-chloro-2,3-di-n-butoxy-1,4-naphthoquinone;
5-chloro-2,3-di-s-butoxy-1,4-naphthoquinone;
6-chloro-2,3-di-s-butoxy-1,4-naphthoquinone;
5-chloro-2,3-di-n-pentyloxy-1,4-naphthoquinone;
6-chloro-2,3-di-n-pentyloxy-1,4-naphthoquinone;
5-chloro-2,3-di-s-pentyloxy-1,4-naphthoquinone;
6-chloro-2,3-di-s-pentyloxy-1,4-naphthoquinone;
5-chloro-2,3-di-n-hexyloxy-1,4-naphthoquinone;
6-chloro-2,3-di-n-hexyloxy-1,4-naphthoquinone;
5-chloro-2,3-di-i-hexyloxy-1,4-naphthoquinone;
6-chloro-2,3-di-i-hexyloxy-1,4-naphthoquinone;
5-chloro-2,3-di(2,2-dimethylpropoxy)-1,4-naphthoquinone;
6-chloro-2,3-di(2,2-dimethylpropoxy)-1,4-naphthoquinone;
2,3,5-trimethoxy-1,4-naphthoquinone;
2,3,6-trimethoxy-1,4-naphthoquinone;
2,3,6-triethoxy-1,4-naphthoquinone;
6-i-butoxy-2,3-dimethoxy-1,4-naphthoquinone;
6-phenylethoxy-2,3-dimethoxy-1,4-naphthoquinone;
6-chloro-2,3-diphenoxy-1,4-naphthoquinone;
6-chloro-2,3-di(4-chlorophenoxy)-1,4-naphthoquinone;
6-chloro-2,3-di(4-methoxyphenoxy)-1,4-naphthoquinone;

6-chloro-2,3-di(2,4-dichlorophenoxy)-1,4-naphthoquinone; and 6-chloro-2,3-di(3-methylphenoxy)-1,4-naphthoquinone.

PREPARATION 5

5-Cyano-2,3-dimethoxy-1,4-naphthoquinone (Preparation of Compounds of Formula (VI) where $R^3$ is cyano)

A solution of sodium nitrite (2.21 g, 32 mmol) in water (6 ml) was added at 0°–5° C. to a stirred suspension of 5-amino-2,3-dimethoxy-1,4-naphthoquinone (3.73 g, 16 mmol) in 3:1 water:tetrahydrofuran (20 ml) containing concentrated hydrochloric acid (6.7 ml) and the resulting mixture was stirred at 0°–5° C. for a further 1¼ hour. The almost clear solution is then neutralized with sodium carbonate, filtered and added at 5° C. to a vigorously stirred solution of cuprous chloride (4.75 g) and sodium cyanide (5.88 g) in water (80 ml). Ethyl acetate (100 ml) was added and the mixture is heated at 45° C. for 0.5 hours, filtered through a celite bed and separated into the two phases. The aqueous phase was extracted with ethyl acetate (2×100 ml). The combined organic phases were extracted with brine (150 ml), dried over MgSO4 and concentrated to dryness in vacuo. The residue was recrystallized from isopropanol giving 2.96 g of 5-cyano-2,3-dimethoxy-1,4-naphthoquinone, mp 171°–172° C.

Similarly, proceeding as above the following compound is prepared:

6-cyano-2,3-dimethoxy-1,4-naphthoquinone.

PREPARATION 6

Di-(2,3-dimethoxy-1,4-naphthoquinone-5)-disulfide (Preparation of Compounds of Formula (VII))

A slurry of potassium thiolacetate (1.5 g, 13.1 mmol) in dimethylformamide (25 ml) was added over 10 minutes to a solution at 0°–5° C. of 5-amino-2,3-dimethoxy-1,4-naphthoquinone (2.63 g, 10 mmol) in dimethylformamide (25 ml). The mixture was allowed to warm to 22° C. and, after 2 hours, an additional quantity of potassium thiolacetate (1.25 g) was added. After a further 45 minute reaction, the mixture was added to ice water (500 ml) that was adjusted to pH 6 with acetic acid. The precipitated solid was filtered off, washed with water and recrystallized from chloroform:methanol (1:1) giving 1.32 g. of di(2,3-dimethoxy-1,4-naphthoquinone-5)-disulfide, mp 220°–221° C.

PREPARATION 7

2,3-Dimethoxy-5-phenylthio-1,4-naphthoquinone (Preparation of Compounds of Formula (VI) where $R^3$ is phenylthio)

Method A. Sodium nitrite (0.18 g) was added at 0°–5° C. to a stirred suspension of 5-amino-2,3-dimethoxy-1,4-naphthoquinone (233 mg, 1 mmol) in 0.6N hydrochloric acid (10 ml) and tetrahydrofuran (1 ml). The mixture was stirred at 5° C. for 10 minutes until a clear solution was obtained and was then neutralized by the addition of sodium carbonate. The ice cold solution was then slowly added to a vigorously stirred two-phase mixture in a nitrogen atmosphere at 50° C. composed of potassium hydroxide (0.16 g), water (10 ml), thiophenol (0.32 ml) and ethyl acetate (35 ml). After a total reaction time of 20 min, the mixture was partitioned between ethyl acetate (40 ml) and brine (100 ml). The ethyl acetate phase was dried over MgSO4 and concentrated in vacuo. The residue was purified by chromatography on a thick layer silica gel plate using acetone:toluene:chloroform (1:20:20) giving a solid that, after recrystallizing from isopropanol, afforded 70 mg of 2,3-dimethoxy-5-phenylthio-1,4-naphthoquinone, mp 76°–77° C.

Similarly, using imidazolyl-2-thiol in place of thiophenol, 2,3-dimethoxy-5-(imidazol-2-yl)thio-1,4-naphthoquinone, mp 97°–100° C., was prepared.

Method B. Thiophenol (6.0 ml, 59 mmol) was added at −30° C. to a stirred mixture of 100% sodium hydride (1.4 g, 59 mmol) and dimethylformamide (200 ml) and the resulting mixture was stirred at 22° C. for 16 hours. This mixture was then cooled to −50° C. and a solution of di(2,3-dimethoxy-1,4-naphthoquinone-5)-disulfide (13.0 g, 49 mmol) in dimethylformamide (100 ml) was added over 30 min. The resulting mixture was allowed to warm to 22° C. over 1 hour before being cooled to −50° C. and neutralized with acetic acid (5.4 ml, 90 mmol). The reaction mixture was then poured into a mixture of water (1.8 l) and methanol (700 ml). The precipitated material was filtered off and recrystallized from methanol giving 10.3 g of 2,3-dimethoxy-5-phenylthio-1,4-naphthoquinone, mp 76°–79° C. A further amount (2.2 g) mp 76°–77° C. was obtained in a second crop from the recrystallization.

Similarly, substituting of the appropriate thiol for thiophenol and the appropriate compound from Preparation 3, the following compounds are prepared:

2,3-dimethoxy-6-(2-chlorophenylthio)-1,4-naphthoquinone;

2,3-dimethoxy-5-(3-chlorophenylthio)-1,4-naphthoquinone, mp 125°–126° C.;

2,3-dimethoxy-6-(4-chlorophenylthio)-1,4-naphthoquinone;

2,3-dimethoxy-5-(2,6-dichlorophenylthio)-1,4-naphthoquinone, mp 158°–159° C.;

2,3-dimethoxy-5-(4-fluorophenylthio)-1,4-naphthoquinone, mp 124°–125° C.;

2,3-dimethoxy-5-(2-bromophenylthio)-1,4-naphthoquinone, mp 152°–153° C.;

2,3-dimethoxy-6-(4-bromophenylthio)-1,4-naphthoquinone;

2,3-diethoxy-6-(4-methoxyphenylthio)-1,4-naphthoquinone;

2,3-di-n-propoxy-6-(4-nitrophenylthio)-1,4-naphthoquinone;

2,3-di-n-butoxy-6-(2-ethylphenylthio)-1,4-naphthoquinone;

2,3-di-n-pentyloxy-6-pyridin-2-ylthio-1,4-naphthoquinone;

2,3-di-n-hexyloxy-6-pyridin-4-ylthio-1,4-naphthoquinone; and 2,3-dimethoxy-5-(4-acetylaminophenylthio)-1,4-naphthoquinone, mp 118°–127° C.

PREPARATION 8

2,3-Dimethoxy-5-methylthio-1,4-naphthoquinone (Preparation of Compounds of Formula (VI) where $R^3$ is methylthio)

Sodium borohydride (100 mg) was added portionwise to a stirred suspension of di(2,3-dimethoxy-1,4-naphthoquinone-5)-disulfide (0.5 g, 1 mmol) in 7:1 tetrahydrofuran:isopropanol (40 ml) in a nitrogen atmosphere until TLC analysis indicated that no starting material remains. Methyl iodide (0.2 ml) was then added and, after 5 minutes, the reaction mixture was poured into ice water (300 ml). 10% Ferric chloride (10 ml) was subsequently added. The precipitated solid was filtered off, washed with water and recrystallized from isopropanol giving 0.36 g of 2,3-dimethoxy-5-methylthio-1,4-naphthoquinone, mp 112°–113° C.

By substituting other alkyl iodides for methyl iodide the following are prepared;
2,3-dimethoxy-6-methylthio-1,4-naphthoquinone;
2,3-dimethoxy-5-benzylthio-1,4-naphthoquinone, m.p. 142°–143° C.;
2,3-dimethoxy-6-ethylthio-1,4-naphthoquinone; and
2,3-dimethoxy-5-methoxycarbonylmethylthio-1,4-naphthoquinone, m.p. 119°–120° C.

PREPARATION 9

2,3-Dimethoxy-5-(4-methylpyridinumthio)-1,4-naphthoquinone methyl sulfate

A mixture of dimethylsulfate (0.19 ml, 2 mmol) and 2,3-dimethoxy-5-(4-methylpyridinylthio)-1,4-naphthoquinone (327 mg, 1 mmol) in tetrahydrofuran (10 ml) was heated under reflux for 3 hours and then cooled to 20° C. The orange solid was filtered off, washed with tetrahydrofuran and recrystallized from ethanol:isopropanol giving 279 mg of 2,3-dimethoxy-5-(4-methylpyridiniumthio)-1,4-naphthoquinone methyl sulfate mp 160°–162° C. and a second crop of 110 mg.

Similarly prepared is 2,3-dimethoxy-5-(2-methylpyridiniumthio)-1,4-naphthoquinone methyl sulfate.

Similarly, the following compounds are prepared by the above method:
2,3-dimethoxy-5-(2-methylpyridiniumsulfinyl)-1,4-naphthoquinone methyl sulfate, m.p. 175°–176° C.; and
2,3-dimethoxy-5-(4-methylpyridiniumsulfinyl)-1,4-naphthoquinone methyl sulfate, m.p. 175°–176° C.

PREPARATION 10

(Preparation of compounds of formula (X) wherein $R^3$ is 6-chloro)

Method A: Into a solution of 6-chloro-1,4-naphthoquinone (193 g) in glacial acetic acid (1600 mL) was bubbled chlorine gas until TLC of an aliquot showed complete disappearance of 6-chloro-1,4-naphthoquinone. The resulting precipitate was collected by filtration, and washed with acetic acid (200 mL) and hexane (2×300 mL) and air dried to yield the 2,3,6-trichloro-2,3-dihydro-1,4-naphthoquinone (157 g). The solid was transferred into a flask equipped with a mechanical stirrer and reflux condenser. Sodium acetate (98.4 g) and acetic acid (1.5 L) were added, and into the suspension was bubbled chlorine gas. The mixture was brought to reflux and maintained there for 2 hours. The cooled mixture was poured over water (3.5 L), and the resulting precipitate was collected by filtration, and was washed with water (2×500 mL), air dried and then vacuum dried over phosphorus pentoxide, to yield 2,3,6-trichloro-1,4-naphthoquinone (139 g), mp 147.5°–148.5° C.

Method B: Into a suspension of 6-chloro-1,4-naphthoquinone (100 g) in acetic acid (800 mL) heated to 70° C. with mechanical stirring was bubbled chlorine gas. Heating was increased to bring the mixture to reflux, at which time solid iodine (13.2 g) was added. Chlorine addition at reflux was continued until TLC showed complete conversion to product, 7–10 hours total. The reaction was cooled to give a thick precipitate of 2,3,6-trichloro-1,4-naphthoquinone collected by filtration. A second crop was obtained by concentration and/or dilution with water. Total yield of dried product was 121.2 g, mp 147.5°–148.5° C.

Similarly, using either of the above procedures, the following compounds, for example, are prepared:
6-bromo-2,3-dichloro-1,4-naphthoquinone;
6-fluoro-2,3-dichloro-1,4-naphthoquinone;
6-methyl-2,3-dichloro-1,4-naphthoquinone;
6-i-propyl-2,3-dichloro-1,4-naphthoquinone;
6-phenyl-2,3-dichloro-1,4-naphthoquinone; and
6-benzyl-2,3-dichloro-1,4-naphthoquinone.

PREPARATION 11

(Preparation of compounds of formula (VI) wherein $R^3$ is 6-chloro)

To a mechanically stirred solution of sodium methoxide (55.5 g) in anhydrous methanol (1.5 L) under a blanket of nitrogen was added 2,3,6-trichloro-1,4-naphthoquinone from Preparation 10 (130 g) as rapidly as possible. The temperature rose to 50° C. during the addition, and the reaction was then heated to reflux for 1 hour. The mixture was cooled and acidified with 6M hydrochloric acid to give a brilliant yellow color. After the addition of water (300 mL), the reaction mixture was filtered, and the precipitate was washed with aqueous methanol (4:1 water-methanol) until the filtrate was yellow-orange. The precipitate was air dried to yield 6-chloro-2,3-dimethoxy-1,4-naphthoquinone (102 g), mp 125°–126 C.

Similarly, using the above procedure, the following compounds are prepared:
6-bromo-2,3-dimethoxy-1,4-naphthoquinone;
6-fluoro-2,3-dimethoxy-1,4-naphthoquinone;
6-chloro-2,3-diethoxy-1,4-naphthoquinone;
6-methyl-2,3-dimethoxy-1,4-naphthoquinone;
6-i-propyl-2,3-dimethoxy-1,4-naphthoquinone;
6-phenyl-2,3-dimethoxy-1,4-naphthoquinone; and
6-benzyl-2,3-dimethoxy-1,4-naphthoquinone.

PREPARATION 12

(Preparation of a compound of formula (VI) wherein $R^1$ and $R^2$ are n-butoxy)

A. To a solution of sodium-n-butoxide (25.8 g) in dry dimethylformamide (125 ml) was added 2,3,6-trichloro-1,4-naphthoquinone (28 g) in one amount. The mixture was refluxed for 2 hours, then cooled, acidified with 6M hydrochloric acid and evaporated. The residue was chromatographed over silica gel using dichloromethane as eluant to yield 2,3-di-n-butoxy-6-chloro-1,4-naphthoquinone (12.3 g) as a red oily solid.

B. Similarly, proceeding as above in Part A, substituting the appropriate compound for 2,3,6-trichloro-1,4-naphthoquinone and the appropriate sodium alkoxide or sodium phenoxide for sodium-n-butoxide, the following compounds are prepared:
6-chloro-2,3-di-i-butoxy-1,4-naphthoquinone;
6-chloro-2,3-(2,2-dimethylpropoxy)-1,4-naphthoquinone;
2,3-di-s-butoxy-1,4-naphthoquinone;
2,3-di(2,2-dimethylpropoxy)-1,4-naphthoquinone;
2,3-di-n-hexyloxy-1,4-naphthoquinone;
2,3-di-n-butoxy-1,4-naphthoquinone;
2,3-diphenoxy-1,4-naphthoquinone;
6-chloro-2,3-diphenoxy-1,4-naphthoquinone;
6-chloro-2,3-di(4-ethylphenoxy)-1,4-naphthoquinone;
6-chloro-2,3-di(2-fluorophenoxy)-1,4-naphthoquinone;
6-chloro-2,3-di(4-t-butylphenoxy)-1,4-naphthoquinone;

6-chloro-2,3-di(2,6-dimethylphenoxy)-1,4-naphthoquinone; and
6-chloro-2,3-di(2-ethoxyphenoxy)-1,4-naphthoquinone.

PREPARATION 13

(Preparation of a compound of formula (VI) wherein $R^3$ is hydrogen)

To a mechanically stirred solution of sodium methoxide (11.1 g) in anhydrous methanol (200 mL) under a blanket of nitrogen was added 2,3-dichloro-1,4-naphthoquinone (22.7 g) as rapidly as possible. The temperature rose to 50° C. during the addition, and the reaction was then heated to reflux for 1 hour. The mixture was cooled and acidified with 6M hydrochloric acid to give a brilliant yellow color. After the addition of water (800 mL), the reaction mixture was filtered, and the precipitate was washed with aqueous methanol (4:1 water-methanol) until the filtrate was yellow-orange. The precipitate was air dried to yield 21.2 g of 2,3-dimethoxy-1,4-naphthoquinone, m.p. 116°–117° C.

Similarly, substituting the appropriate sodium alkoxide for sodium methoxide the following compounds are prepared.
2,3-diethoxy-1,4-naphthoquinone;
2,3-di-n-propoxy-1,4-naphthoquinone;

PREPARATION 14

(Preparation of a compound of formula (XII) wherein W is methyl)

A. A solution of 6-chloro-2,3-dimethoxy-1,4-naphthoquinone (50.5 g, 200 mmol) in tetrahydrofuran (500 mL) was hydrogenated at atmospheric pressure over palladium-on-charcoal (10%, 5.0 g) until the solution was colorless, approximately 4 hours.

B. While still under a blanket of hydrogen, a solution of acetic anhydride (47 mL) pyridine (40 mL) and DMAP (1.22 g) in tetrahydrofuran (50 mL) was added to the mixture. After stirring for 1 hour, the mixture was filtered and evaporated. The residue was dissolved in ether (500 mL) and was washed with 1M HCl (3×250 mL) and with brine (2×250 mL). The organic layer was dried over sodium sulfate, filtered, and evaporated to give an oil which crystallized at high vacuum. Recrystallization from ether-petroleum ether afforded 6-chloro-1,4-diacetyloxy-2,3-dimethoxynaphthalene, m.p. 93°–94° C.

Similarly, using the above procedure substituting the appropriate compound of formula (VI) for 6-chloro-2,3-dimethoxy-1,4-naphthoquinone, where appropriate, and the appropriate acid anhydride for acetic anhydride, where appropriate, the following compounds are prepared:
6-chloro-2,3-dimethoxy-1,4-di-n-propanoyloxynaphthalene, m.p. 84°–85° C.;
6-chloro-2,3-dimethoxy-1,4-di-i-butanoyloxynaphthalene, m.p. 64°–65° C.;
6-chloro-2,3-dimethoxy-1,4-di(2,2-dimethylpropanoyloxy)naphthalene, m.p. 132°–133° C.;
6-chloro-2,3-dimethoxy-1,4-di-n-octanoyloxynaphthalene;
6-chloro-2,3-di-n-butoxy-1,4-diacetyloxynaphthalene, m.p. 74°–75° C.;
6-chloro-2,3-di-s-butoxy-1,4-diacetyloxynaphthalene;
6-chloro-2,3-di(2,2-dimethylpropoxy)-1,4-diacetyloxynaphthalene;
2,3-di-n-butoxy-1,4-di-n-pentanoyloxynaphthalene;
6-chloro-2,3-di-n-propoxy-1,4-dipropanoyloxynaphthalene, m.p. 39°–40° C.;
6-chloro-2,3-di-i-propoxy-1,4-dioctanoyloxynaphthalene;
6-bromo-2,3-dimethoxy-1,4-diacetyloxynaphthalene, m.p. 102°–103° C.;
6-fluoro-2,3-dimethoxy-1,4-diacetyloxynaphthalene, m.p. 102°–103° C.;
5-chloro-2,3-dimethoxy-1,4-diacetyloxynaphthalene, m.p. 133°–135° C.;
5-cyano-2,3-dimethoxy-1,4-diacetyloxynaphthalene, m.p. 152°–153° C.;
6-cyano-2,3-dimethoxy-1,4-diacetyloxynaphthalene, m.p. 124°–125° C.;
6-methylamino-2,3-dimethoxy-1,4-diacetyloxynaphthalene;
6-diethylamino-2,3-dimethoxy-1,4-dipropanoyloxynaphthalene;
6-ethylmethylamino-2,3-dimethoxy-1,4-di-n-butanoyloxynaphthalene;
2,3,6-trimethoxy-1,4-di-n-pentanoyloxynaphthalene;
2,3,6-triethoxy-1,4-di-n-hexanoyloxynaphthalene;
6-i-butoxy-2,3-dimethoxy-1,4-di(2,2-dimethylpropanoyloxy)naphthalene;
6-phenylethoxy-2,3-dimethoxy-1,4-diacetyloxynaphthalene;
6-methyl-2,3-dimethoxy-1,4-diacetyloxynaphthalene, m.p. 70°–71° C.;
6-i-propyl-2,3-dimethoxy-1,4-di-n-octanoyloxynaphthalene;
6-phenyl-2,3-dimethoxy-1,4-diacetyloxynaphthalene;
6-benzyl-2,3-dimethoxy-1,4-dipropanoyloxynaphthalene;
5-chloro-2,3-di-n-pentyloxy-1,4-di-n-butanoyloxynaphthalene;
5-chloro-2,3-di-s-pentyloxy-1,4-diacetyloxynaphthalene;
5-chloro-2,3-di-n-hexyloxy-1,4-di-n-octanoyloxynaphthalene;
5-chloro-2,3-di-i-hexyloxy-1,4-diacetyloxynaphthalene;
5-chloro-2,3-dimethoxy-1,4-di(2,2-dimethylpropanoyloxynaphthalene, m.p. 128°–130° C.;
6-chloro-2,3-dimethoxy-1,4-di-ni-butanoyloxynaphthalene, oil;
6-chloro-2,3-diethoxy-1,4-diacetyloxynaphthalene, m.p. 91°–92° C.;
6-chloro-2,3-diethoxy-1,4-di-n-propanoyloxy-naphthalene, m.p. 81°–82° C.;
6-chloro-2,3-diethoxy-1,4-di-i-butanoyloxynaphthalene, m.p. 77°–78° C.;
6-chloro-2,3-diethoxy-1,4-di(2,2-dimethylpropanoyloxy)naphthalene, m.p. 104°–105° C.;
6-chloro-2,3-di-n-propoxy-1,4-di-i-butanoyloxynaphthalene, m.p. 51°–52° C.;
6-chloro-2,3-di-n-propoxy-1,4-di(2,2-dimethylpropanoyloxy)naphthalene, m.p. 59°–60° C.;
2,3,5-trimethoxy-1,4-diacetyloxynaphthalene, m.p. 69°–70° C.;
2,3,5-trimethoxy-1,4-di-n-propanoyloxynaphthalene, m.p. 72°–73° C.;
2,3,5-trimethoxy-1,4-di(2,2-dimethylpropanoyloxy)-naphthalene, m.p. 153°–154° C.;
2,3,6-trimethoxy-1,4-di-n-propanoyloxynaphthalene, m.p. 86°–87° C.;
2,3,6-trimethoxy-1,4-di(2,2-dimethylpropanoyloxy)-naphthalene, amorphous;
6-chloro-2,3-di-n-propoxy-1,4-diacetyloxynaphthalene, m.p. 53°–54° C.;

6-chloro-2,3-di-i-propoxy-1,4-diacetyloxynaphthalene, m.p. 132°–133° C.;
6-chloro-2,3-di-i-propoxy-1,4-di-n-butanoyloxynaphthalene, oil;
6-chloro-2,3-di-i-propoxy-1,4-i-butanoyloxynaphthalene, oil;
6-chloro-2,3-di-i-propoxy-1,4-di(2,2-dimethylpropanoyloxy)naphthalene, m.p. 137°–138° C.;
2,3,6-trimethoxy-1,4-diacetyloxynaphthalene, m.p. 77°–78° C.;
5-methyl-2,3-dimethoxy-1,4-diacetyloxynaphthalene, m.p. 114°–115° C.;
5-methyl-2,3-dimethoxy-1,4-di-n-propanoyloxynaphthalene, m.p. 91°–92° C.;
5-methyl-2,3-dimethoxy-1,4-di-i-butanoyloxynaphthalene, m.p. 130°–131° C.;
5-methyl-2,3-dimethoxy-1,4-di(2,2-dimethylpropanoyloxy)naphthalene, m.p. 80°–81° C.;
6-methyl-2,3-dimethoxy-1,4-di-n-propanoyloxynaphthalene, m.p. 57°–58° C.;
6-methyl-2,3-dimethoxy-1,4-di-i-butanoyloxynaphthalene, oil;
6-methyl-2,3-dimethoxy-1,4-di(2,2-dimethylpropanoyloxy)naphthalene, m.p. 110°–111° C.;
6,7-dimethyl-2,3-dimethoxy-1,4-di-acetyloxynaphthalene, m.p. 124°–125° C.;
6,7-dimethyl-2,3-dimethoxy-1,4-di-n-propanoyloxynaphthalene, m.p. 108°–109° C.;
6,7-dimethyl-2,3-dimethoxy-1,4-di-n-butanoyloxynaphthalene, m.p. 69°–70° C.;
6,7-dimethyl-2,3-dimethoxy-1,4-di-i-butanoyloxynaphthalene, m.p. 98°–99° C.;
6,7-dimethyl-2,3-dimethoxy-1,4-di(2,2-dimethylpropanyloxy)naphthalene, m.p. 124°–125° C.;
2,3-dimethoxy-1,4-dibenzoyloxynaphthalene;
6-chloro-2,3-dimethoxy-1,4-dibenzoyloxynaphthalene; m.p. 161°–162° C.
6-chloro-2,3-diethoxy-1,4-di(2-chlorobenzoyloxy)naphthalene;
6-chloro-2,3-diethoxy-1,4-di(3-bromobenzoyloxy)naphthalene;
6-chloro-2,3-di-n-propoxy-1,4-di(4-ethylbenzoyloxy)naphthalene;
6-chloro-2,3-di-n-propoxy-1,4-di(4-fluorobenzoyloxy)naphthalene;
6-chloro-2,3-diethoxy-1,4-di(2-methoxybenzoyloxy)naphthalene;
6-chloro-2,3-diethoxy-1,4-di(4-ethoxybenzoyloxy)naphthalene;
6-chloro-2,3-di-n-butyloxy-1,4-di(2,4-dichlorobenzoyloxy)naphthalene;
6-chloro-2,3-di-n-butyloxy-1,4-di(3,5-dichlorobenzoyloxy)naphthalene;
6-chloro-2,3-dimethoxy-1,4-di(2,6-dimethylbenzoyloxy)naphthalene;
2,3-dimethoxy-1,4-diphenylacetyloxynaphthalene;
6-chloro-2,3-dimethoxy-1,4-diphenylacetyloxynaphthalene;
6-chloro-2,3-diethoxy-1,4-di(2-chlorophenylacetyloxy)naphthalene;
6-chloro-2,3-diethoxy-1,4-di(4-fluorophenylacetyloxy)naphthalene;
6-chloro-2,3-di-n-propoxy-1,4-di(2-methoxyphenylacetyloxy)naphthalene;
6-chloro-2,3-di-n-propoxy-1,4-di(4-methoxyphenylacetyloxy)naphthalene;
6-chloro-2,3-di-n-propoxy-1,4-di(4-ethoxyphenylacetyloxy)naphthalene;
6-chloro-2,3-dimethoxy-1,4-di(2-methylphenylacetyloxy)naphthalene;
6-chloro-2,3-dimethoxy-1,4-di(4-ethylphenylacetyloxy)naphthalene;
2,3-diphenoxy-1,4-diacetyloxynaphthalene;
6-chloro-2,3-diphenoxy-1,4-dibenzoyloxynaphthalene, m.p. 173°–174° C.;
6-chloro-2,3-diphenoxy-1,4-diacetyloxynaphthalene; m.p. 144°–145° C.;
6-chloro-2,3-di(2-chlorophenoxy)-1,4-dibenzoyloxynaphthalene;
6-chloro-2,3-diphenoxy-1,4-di-n-propanoyloxynaphthalene, m.p. 136°–137° C.;
6-chloro-2,3-diphenoxy-1,4-di-n-butanoyloxynaphthalene, m.p. 109°–110° C.;
6-chloro-2,3-di(4-chlorophenoxy)-1,4-di(4-benzoyloxynaphthalene;
6-chloro-2,3-di(4-methoxyphenoxy)-1,4-diphenylacetyloxynaphthalene;
6-chloro-2,3-di(2,4-dichlorophenoxy)-1,4-diphenylacetyloxynaphthalene;
6-chloro-2,3-di(3-methylphenoxy)-1,4-diacetyloxynaphthalene;
6-chloro-2,3-di(4-ethylphenoxy)-1,4-dibenzyloxynaphthalene; and
6-chloro-2,3-di(2-fluorophenoxy)-1,4-di(2-methylbenzoyloxy)naphthalene.

PREPARATION 15

(Preparation of a compound of formula (XII) wherein W is methyl)

A solution of 2,3-dimethoxy-1,4-naphthoquinone (20.0 g) in tetrahydrofuran (150 mL) was hydrogenated at atmospheric pressure over Pd-C (10%, 0.5 g) until the solution was colorless, approximately 4 hours. While still under a blanket of hydrogen, a solution of acetic anhydride (20 mL) and pyridine (18 mL) in tetrahydrofuran (50 mL) was added to the mixture. After stirring for 1 hour, the mixture was evaporated. The residue was dissolved in ether (100 mL) and was washed with 1M hydrochloric acid (3×50 mL) and with brine (2×50 mL). The organic layer was dried over sodium sulfate, filtered, and evaporated. Recrystallization from ether afforded 2,3-dimethoxy-1,4-diacetyloxynaphthalene (22.5 g), m.p. 138°–139° C.

Similarly proceeding as above, substituting the appropriate compound for 2,3-dimethoxy-1,4-naphthoquinone, where appropriate, and the appropriate acid anhydride, where appropriate, for acetic anhydride, the following compounds, for example, are prepared:
2,3-di-n-propoxy-1,4-di-n-propanoyloxynaphthalene;
2,3-di-s-butoxy-1,4-di-i-butanoyloxynaphthalene;
2,3-di(2,2-dimethylpropoxy)-1,4-di-n-pentanoyloxynaphthalene;
2,3-di-n-hexyloxy-1,4-di(2,2-dimethylpropanoyloxy)naphthalene;
2,3-dimethoxy-1,4-di-n-propanoyloxynaphthalene, m.p. 111°–112° C.;
2,3-diethoxy-1,4-diacetyloxynaphthalene;
2,3-dimethoxy-1,4-di-n-butanoyloxynaphthalene, m.p. 53°–54° C.;
2,3-dimethoxy-1,4-di-i-butanoyloxynaphthalene, m.p. 95°–96° C.; and
2,3-dimethoxy-1,4-di(2,2-dimethylpropanoyloxy)naphthalene, m.p. 178°–180° C.

PREPARATION 16

(Preparation of Compounds of formula (XII) where $R^3$ is phenylsulfinyl)

Forty percent (w/v) peracetic acid in acetic acid (1 ml) is added over 30 minutes to a solution of 2,3-dimethoxy-5-phenylthio-1,4-diacetyloxynaphthalene (0.98 g, 3 mmol) in methylene chloride (15 ml). Excess peracetic acid is destroyed by the addition of a few milligrams of 5% palladium on carbon and the mixture filtered through a celite bed. The filtrate is concentrated in vacuo and the residue recrystallized from methanol giving 0.59 g of 2,3-dimethoxy-5-phenylsulfinyl-1,4-diacetyloxynaphthalene.

Similarly, using either peracetic acid or m-chloroperbenzoic acid, the following compounds are prepared from the respective thio compounds:

2,3-dimethoxy-5-(imidazol-2-ylsulfinyl)-1,4-diacetyloxynaphthalene;
2,3-dimethoxy-6-(2-chlorophenylsulfinyl)-1,4-diacetyloxynaphthalene;
2,3-dimethoxy-5-(3-chlorophenylsulfinyl)-1,4-diacetyloxynaphthalene;
2,3-dimethoxy-6-(4-chlorophenylsulfinyl)-1,4-diacetyloxynaphthalene;
2,3-dimethoxy-5-(2,6-dichlorophenylsulfinyl)-1,4-diacetyloxynaphthalene;
2,3-dimethoxy-5-(4-fluorophenylsulfinyl)-1,4-diacetyloxynaphthalene;
2,3-dimethoxy-5-(2-bromophenylsulfinyl)-1,4-diacetyloxynaphthalene;
2,3-dimethoxy-5-(4-bromophenylsulfinyl)-1,4-diacetyloxynaphthalene;
2,3-diethoxy-6-(4-methoxyphenylsulfinyl)-1,4-diacetyloxynaphthalene;
2,3-dipropoxy-6-(4-nitrophenylsulfinyl)-1,4-diacetyloxynphthalene;
2,3-di-n-butoxy-6-(2-ethylphenylsulfinyl)-1,4-diacetyloxynaphthalene;
2,3-dimethoxy-6-(pyrimidin-2-ylsulfinyl)-1,4-diacetyloxynaphthalene;
2,3-dimethoxy-5-(pyrimidin-4-ylsulfinyl)-1,4-diacetyloxynaphthalene;
2,3-dimethoxy-6-methylsulfinyl-1,4-diacetyloxynaphthalene;
2,3-dimethoxy-5-benzylsulfinyl-1,4-diacetyloxynaphthalene; and
2,3-dimethoxy-5-methoxycarbonylmethylsulfinyl-1,4-diacetyloxynaphthalene.

PREPARATION 17

2,3-Dimethoxy-5-phenylsulfonyl-1,4-diacetyloxynaphthalene (Preparation of Compound of formula (XII) where $R^3$ is phenylsulfonyl)

A mixture of m-chloroperbenzoic acid (300 mg) and 2,3-dimethoxy-5-phenylthio-1,4-naphthoquinone (200 mg, 0.61 mmol) in methylene chloride (5 ml) is stirred at 22° C. for 16 hours and the resulting solution then passed through an alumina column (10 g of Activity 1) eluting with chloroform. The eluates are concentrated to dryness and the residue is crystallized from isopropanol giving 95 mg of 2,3-dimethoxy-5-phenylsulfonyl-1,4-diacetyloxynaphthalene.

EXAMPLE I (Preparation of a compound of formula (Ia))

A. Ten grams of 6-chloro-2,3-dimethoxy-1,4-diacetyloxynaphthalene, 150 ml of 0.05M, pH 8, phosphate buffer solution and 150 ml of acetonitrile were heated at 80° C. for 10 days. The reaction was monitored by TLC. Additional disodium hydrogen phosphate was added to maintain the reaction mixture at pH 8. The reaction mixture was cooled and solvent evaporated and the resultant residue was extracted with ethyl acetate (3X), washed with 1M HCl (2X) and brine (2X). The solution was dried over sodium sulfate, filtered and evaporated. The residue which is an isomeric mixture was recrystallized from petroleum ether and gave 2.0 gm 6-chloro-2,3-dimethoxy-1-acetyloxy-4-hydroxynaphthalene, m.p. 155°–6° C.

B. 6-Chloro-2,3-dimethoxy-4-acetyloxy-1-hydroxynaphthalene was obtained by evaporation of the petroleum ether solution followed by preparative HPLC using silica gel eluted with 4% anhydrous methanol in hexane, m.p. 106°–107° C.

C. Similarly, proceeding as in Part A above, substituting the appropriate compound for 6-chloro-1,4-diacetyloxy-2,3-dimethoxynaphthalene the following compounds, for example, are prepared:

6-chloro-2,3-dimethoxy-1-hydroxy-4-n-propanoyloxynaphthalene;
6-chloro-2,3-dimethoxy-1-hydroxy-4-i-butanoyloxynaphthalene;
6-chloro-2,3-dimethoxy-1-hydroxy-4-(2,2-dimethylpropanoyl-oxy)naphthalene;
6-chloro-2,3-dimethoxy-1-hydroxy-4-n-octanoyloxynaphthalene;
6-chloro-2,3-di-n-butoxy-1-hydroxy-4-acetyloxynaphthalene;
6-chloro-2,3-di-s-butoxy-1-hydroxy-4-acetyloxynaphthalene;
6-chloro-2,3-di(2,2-dimethylpropoxy)-1-hydroxy-4-acetyloxy-naphthalene;
2,3-di-n-butoxy-1-hydroxy-4-n-pentanoyloxynaphthalene;
6-chloro-2,3-di-n-propoxy-1-hydroxy-4-propanoyloxynaphthalene;
6-chloro-2,3-di-i-propoxy-1-hydroxy-4-octanoyloxynaphthalene;
6-bromo-2,3-dimethoxy-1-hydroxy-4-acetyloxynaphthalene;
6-fluoro-2,3-dimethoxy-1-hydroxy-4-acetyloxynaphthalene;
5-chloro-2,3-dimethoxy-1-hydroxy-4-acetyloxynaphthalene;
2,3-dimethoxy-1-hydroxy-4-(2,2-dimethylpropanoyloxy)naphthalene;
5-cyano-2,3-dimethoxy-1-hydroxy-4-acetyloxynaphthalene;
6-cyano-2,3-dimethoxy-1-hydroxy-4-acetyloxynaphthalene;
6-methylamino-2,3-dimethoxy-1-hydroxy-4-acetyloxynaphthalene;
6-diethylamino-2,3-dimethoxy-1-hydroxy-4-propanoyloxynaphthalene;
6-ethylmethylamino-2,3-dimethoxy-1-hydroxy-4-n-butanoyloxynaphthalene;
2,3,6-trimethoxy-1-hydroxy-4-n-pentanoyloxynaphthalene;

2,3,6-triethoxy-1-hydroxy-4-n-hexanoyloxynaphthalene;
6-i-butoxy-2,3-dimethoxy-1-hydroxy-4-(2,2-dimethylpropanoyloxy)naphthalene;
6-phenylethoxy-2,3-dimethoxy-1-hydroxy-4-acetyloxynaphthalene;
6-methyl-2,3-dimethoxy-1-hydroxy-4-acetyloxynaphthalene;
6-i-propyl-2,3-dimethoxy-1-hydroxy-4-n-octanoyloxynaphthalene;
6-phenyl-2,3-dimethoxy-1-hydroxy-4-acetyloxynaphthalene;
6-benzyl-2,3-dimethoxy-1-hydroxy-4-propanoyloxynaphthalene;
5-chloro-2,3-di-n-pentyloxy-1-hydroxy-4-n-butanoyloxynaphthalene;
5-chloro-2,3-di-s-pentyloxy-1-hydroxy-4-acetyloxynaphthalene;
5-chloro-2,3-di-n-hexyloxy-1-hydroxy-4-n-octanoyloxynaphthalene;
5-chloro-2,3-di-i-hexyloxy-1-hydroxy-4-acetyloxynaphthalene;
5-chloro-2,3-dimethoxy-1-hydroxy-4-(2,2-dimethylpropanoyloxynaphthalene
6-chloro-2,3-dimethoxy-1-hydroxy-4-n-butanoyloxynaphthalene;
6-chloro-2,3-diethoxy-1-hydroxy-4-acetyloxynaphthalene;
6-chloro-2,3-diethoxy-1-hydroxy-4-n-propanoyloxynaphthalene;
6-chloro-2,3-diethoxy-1-hydroxy-4-i-butanoyloxynaphthalene;
6-chloro-2,3-diethoxy-1-hydroxy-4-(2,2-dimethylpropanoyloxy)naphthalene;
6-chloro-2,3-di-n-propoxy-1-hydroxy-4-i-butanoyloxynaphthalene;
6-chloro-2,3-di-n-propoxy-1-hydroxy-4-(2,2-dimethylpropanoyloxy)naphthalene;
2,3,5-trimethoxy-1-hydroxy-4-acetyloxynaphthalene;
2,3,5-trimethoxy-1-hydroxy-4-n-propanoyloxynaphthalene;
2,3,5-trimethoxy-1-hydroxy-4-(2,2-dimethylpropanoyloxy)naphthalene;
2,3,6-trimethoxy-1-hydroxy-4-n-propanoyloxynaphthalene;
2,3,6-trimethoxy-1-hydroxy-4-(2,2-dimethylpropanoyloxy)naphthalene;
6-chloro-2,3-di-n-propoxy-1-hydroxy-4-acetyloxynaphthalene;
6-chloro-2,3-di-i-propoxy-1-hydroxy-4-acetyloxynaphthalene;
6-chloro-2,3-di-i-propoxy-1-hydroxy-4-n-butanoyloxynaphthalene;
6-chloro-2,3-di-i-propoxy-1-hydroxy-4-i-butanoyloxynaphthalene;
6-chloro-2,3-di-i-propoxy-1-hydroxy-4-(2,2-dimethylpropanoyloxy)naphthalene;
2,3,6-trimethoxy-1-hydroxy-4-acetyloxynaphthalene;
5-methyl-2,3-dimethoxy-1-hydroxy-4-acetyloxynaphthalene;
5-methyl-2,3-dimethoxy-1-hydroxy-4-n-propanoyloxynaphthalene;
5-methyl-2,3-dimethoxy-1-hydroxy-4-i-butanoyloxynaphthalene;
5-methyl-2,3-dimethoxy-1-hydroxy-4-(2,2-dimethylpropanoyloxy)naphthalene;
6-methyl-2,3-dimethoxy-1-hydroxy-4-n-propanoyloxynaphthalene;
6-methyl-2,3-dimethoxy-1-hydroxy-4-i-butanoyloxynaphthalene;
6-methyl-2,3-dimethoxy-1-hydroxy-4-(2,2-dimethylpropanoyloxy)naphthalene;
6,7-dimethyl-2,3-dimethoxy-1-hydroxy-4-acetyloxynaphthalene;
6,7-dimethyl-2,3-dimethoxy-1-hydroxy-4-n-propanoyloxynaphthalene;
6,7-dimethyl-2,3-dimethoxy-1-hydroxy-4-n-butanoyloxynaphthalene;
6,7-dimethyl-2,3-dimethoxy-1-hydroxy-4-i-butanoyloxynaphthalene;
6,7-dimethyl-2,3-dimethoxy-1-hydroxy-4-(2,2-dimethylpropanyloxy)naphthalene;
2,3-dimethoxy-1-hydroxy-4-benzoyloxynaphthalene;
6-chloro-2,3-dimethoxy-1-hydroxy-4-benzoyloxynaphthalene;
6-chloro-2,3-diethoxy-1-hydroxy-4-(2-chlorobenzoyloxy)naphthalene;
6-chloro-2,3-diethoxy-1-hydroxy-4-(3-bromobenzoyloxy)naphthalene;
6-chloro-2,3-di-n-propoxy-1-hydroxy-4-(4-ethylbenzoyloxy)naphthalene;
6-chloro-2,3-di-n-propoxy-1-hydroxy-4-(4-fluorobenzoyloxy)naphthalene;
6-chloro-2,3-diethoxy-1-hydroxy-4-(2-methoxybenzoyloxy)naphthalene;
6-chloro-2,3-diethoxy-1-hydroxy-4-(4-ethoxybenzoyloxy)naphthalene;
6-chloro-2,3-di-n-butyloxy-1-hydroxy-4-(2-hydroxy-4-chlorobenzoyloxy)naphthalene;
6-chloro-2,3-di-n-butyloxy-1-hydroxy-4-(3,5-dichlorobenzoyloxy)naphthalene;
6-chloro-2,3-dimethoxy-1-hydroxy-4-(2,6-dimethylbenzoyloxy)naphthalene;
2,3-dimethoxy-1-hydroxy-4-phenylacetyloxynaphthalene;
6-chloro-2,3-dimethoxy-1-hydroxy-4-phenylacetyloxynaphthalene;
6-chloro-2,3-diethoxy-1-hydroxy-4-(2-chlorophenylacetyloxynaphthalene;
6-chloro-2,3-diethoxy-1-hydroxy-4-(4-fluorophenylacetyloxynaphthalene;
6-chloro-2,3-di-n-propoxy-1-hydroxy-4-(2-methoxyphenylacetyloxy)naphthalene;
6-chloro-2,3-di-n-propoxy-1-hydroxy-4-(4-methoxyphenylacetyloxy)naphthalene;
6-chloro-2,3-di-n-propoxy-1-hydroxy-4-(4-ethoxyphenylacetyloxy)naphthalene;
6-chloro-2,3-dimethoxy-1-hydroxy-4-(2-methylphenylacetyloxy)naphthalene;
6-chloro-2,3-dimethoxy-1-hydroxy-4-(4-ethylphenylacetyloxy)naphthalene;
2,3-dimethoxy-1-hydroxy-4-acetyloxynaphthalene;
6-chloro-2,3-diphenoxy-1-hydroxy-4-acetyloxynaphthalene;
6-chloro-2,3-di(2-chlorophenoxy)-1-hydroxy-4-benzoyloxynaphthalene;
6-chloro-2,3-diphenoxy-1-hydroxy-4-n-propanoyloxynaphthalene;
6-chloro-2,3-diphenoxy-1-hydroxy-4-n-butanoyloxynaphthalene;
6-chloro-2,3-di(4-chlorophenoxy)-1-hydroxy-4-benzoyloxynaphthalene;
6-chloro-2,3-di(4-methoxyphenoxy)-1-hydroxy-4-phenylacetyloxynaphthalene;
6-chloro-2,3-di(2-hydroxy-4-chlorophenoxy)-1-hydroxy-4-phenylacetyloxynaphthalene;

6-chloro-2,3-di(3-methylphenoxy)-1-hydroxy-4-acetyloxynaphthalene;
6-chloro-2,3-di(4-ethylphenoxy)-1-hydroxy-4-benzyloxynaphthalene;
6-chloro-2,3-di(2-fluorophenoxy)-1-hydroxy-4-(2-methylbenzoyloxy)naphthalene;
2,3-diethoxy-1-hydroxy-4-acetyloxynaphthalene;
2,3-dimethoxy-1-hydroxy-4-propanoyloxynaphthalene;
2,3-dimethoxy-5-(imidazol-2-ylsulfinyl)-1-hydroxy-4-acetyloxynaphthalene;
2,3-dimethoxy-6-(2-chlorophenylsulfinyl)-1-hydroxy-4-acetyloxynaphthalene;
2,3-dimethoxy-5-(3-chlorophenylsulfinyl)-1-hydroxy-4-acetyloxynaphthalene;
2,3-dimethoxy-6-(4-chlorophenylsulfinyl)-1-hydroxy-4-acetyloxynaphthalene;
2,3-dimethoxy-5-(2,6-dichlorophenylsulfinyl)-1-hydroxy-4-acetyloxynaphthalene;
2,3-dimethoxy-5-(4-fluorophenylsulfinyl)-1-hydroxy-4-acetyloxynaphthalene;
2,3-dimethoxy-5-(2-bromophenylsulfinyl)-1-hydroxy-4-acetyloxynaphthalene;
2,3-dimethoxy-5-(4-bromophenylsulfinyl)-1-hydroxy-4-acetyloxynaphthalene;
2,3-diethoxy-6-(4-methoxyphenylsulfinyl)-1-hydroxy-4-acetyloxynaphthalene;
2,3-dipropoxy-6-(4-nitrophenylsulfinyl)-1-hydroxy-4-acetyloxynaphthalene;
2,3-di-n-butoxy-6-(2-ethylphenylsulfinyl)-1-hydroxy-4-acetyloxynaphthalene;
2,3-dimethoxy-6-(pyrimidin-2-ylsulfinyl)-1-hydroxy-4-acetyloxynaphthalene;
2,3-dimethoxy-5-(pyrimidin-4-ylsulfinyl)-1-hydroxy-4-acetyloxynaphthalene;
2,3-dimethoxy-6-methylsulfinyl-1-hydroxy-4-acetyloxynaphthalene;
2,3-dimethoxy-5-benzylsulfinyl-1-hydroxy-4-acetyloxynaphthalene; and
2,3-dimethoxy-5-methoxycarbonylmethylsulfinyl-1-hydroxy-4-acetyloxynaphthalene.

D. Similarly, proceeding as in Part B above, the following compounds, for example, are prepared:
6-chloro-2,3-dimethoxy-4-hydroxy-1-n-propanoyloxynaphthalene;
6-chloro-2,3-dimethoxy-4-hydroxy-1-i-butanoyloxynaphthalene;
6-chloro-2,3-dimethoxy-4-hydroxy-1-(2,2-dimethylpropanoyloxy)naphthalene;
6-chloro-2,3-dimethoxy-4-hydroxy-1-n-octanoyloxynaphthalene;
6-chloro-2,3-di-n-butoxy-4-hydroxy-1-acetyloxynaphthalene;
6-chloro-2,3-di-s-butoxy-4-hydroxy-1-acetyloxynaphthalene;
6-chloro-2,3-di(2,2-dimethylpropoxy)-4-hydroxy-1-acetyloxynaphthalene;
2,3-di-n-butoxy-4-hydroxy-1-n-pentoyloxynaphthalene;
6-chloro-2,3-di-n-propoxy-4-hydroxy-1-propanoyloxynaphthalene;
6-chloro-2,3-di-i-propoxy-4-hydroxy-1-octanoyloxynaphthalene;
6-bromo-2,3-dimethoxy-4-hydroxy-1-acetyloxynaphthalene;
6-fluoro-2,3-dimethoxy-4-hydroxy-1-acetyloxynaphthalene;
5-chloro-2,3-dimethoxy-4-hydroxy-1-acetyloxynaphthalene;
5-cyano-2,3-dimethoxy-4-hydroxy-1-acetyloxynaphthalene;
6-cyano-2,3-dimethoxy-4-hydroxy-1-acetyloxynaphthalene;
6-methylamino-2,3-dimethoxy-4-hydroxy-1-acetyloxynaphthalene;
6-diethylamino-2,3-dimethoxy-4-hydroxy-1-propanoyloxynaphthlene;
6-ethylmethylamino-2,3-dimethoxy-4-hydroxy-1-n-butanoyloxynaphthalene;
2,3,6-trimethoxy-4-hydroxy-1-n-pentanoyloxynaphthalene;
2,3,6-triethoxy-4-hydroxy-1-n-hexanoyloxynaphthalene;
6-i-butoxy-2,3-dimethoxy-4-hydroxy-1-(2,2-dimethylpropanoyloxy)naphthalene;
6-phenylethoxy-2,3-dimethoxy-4-hydroxy-1-acetyloxynaphthalene;
6-methyl-2,3-dimethoxy-4-hydroxy-1-acetyloxynaphthalene;
6-i-propyl-2,3-dimethoxy-4-hydroxy-1-n-octanoyloxynaphthalene;
6-phenyl-2,3-dimethoxy-4-hydroxy-1-acetyloxynaphthalene;
6-benzyl-2,3-dimethoxy-4-hydroxy-1-propanoyloxynaphthalene;
5-chloro-2,3-di-n-pentyloxy-4-hydroxy-1-n-butanoyloxynaphthalene;
5-chloro-2,3-di-s-pentyloxy-4-hydroxy-1-acetyloxynaphthalene;
5-chloro-2,3-di-n-hexyloxy-4-hydroxy-1-n-octanoyloxynaphthalene;
5-chloro-2,3-di-i-hexyloxy-4-hydroxy-1-acetyloxynaphthalene;
5-chloro-2,3-dimethoxy-4-hydroxy-1-(2,2-dimethylpropanoyloxynaphthalene;
6-chloro-2,3-dimethoxy-4-hydroxy-1-n-butanoyloxynaphthalene;
6-chloro-2,3-diethoxy-4-hydroxy-1-acetyloxynaphthalene;
6-chloro-2,3-diethoxy-4-hydroxy-1-n-propanoyloxynaphthalene;
6-chloro-2,3-diethoxy-4-hydroxy-1-i-butanoyloxynaphthalene;
6-chloro-2,3-diethoxy-4-hydroxy-1-(2,2-dimethylpropanoyloxy)naphthalene;
6-chloro-2,3-di-n-propoxy-4-hydroxy-1-i-butanoyloxynaphthalene;
6-chloro-2,3-di-n-propoxy-4-hydroxy-1-(2,2-dimethylpropanoyloxy)naphthalene;
2,3,6-trimethoxy-4-hydroxy-1-acetyloxynaphthalene;
2,3,6-trimethoxy-4-hydroxy-1-n-propanoyloxynaphthalene;
2,3,5-trimethoxy-4-hydroxy-1-(2,2-dimethylpropanoyloxy)naphthalene;
2,3,6-trimethoxy-4-hydroxy-1-n-propanoyloxynaphthalene;
2,3,6-trimethoxy-4-hydroxy-1-(2,2-dimethylpropanoyloxy)naphthalene;
6-chloro-2,3-di-n-propoxy-4-hydroxy-1-acetyloxynaphthalene;
6-chloro-2,3-di-i-propoxy-4-hydroxy-1-acetyloxynaphthalene;
6-chloro-2,3-di-i-propoxy-4-hydroxy-1-n-butanoyloxynaphthalene;
6-chloro-2,3-di-i-propoxy-4-hydroxy-1-i-butanoyloxynaphthalene;

6-chloro-2,3-di-i-propoxy-4-hydroxy-1-(2,2-dimethylpropanoyloxy)naphthalene;
2,3,6-trimethoxy-4-hydroxy-1-acetyloxynaphthalene;
5-methyl-2,3-dimethoxy-4-hydroxy-1-acetyloxynaphthalene;
5-methyl-2,3-dimethoxy-4-hydroxy-1-n-propanoyloxynaphthalene;
5-methyl-2,3-dimethoxy-4-hydroxy-1-i-butanoyloxynaphthalene;
5-methyl-2,3-dimethoxy-4-hydroxy-1-(2,2-dimethylpropanoyloxy)naphthalene;
6-methyl-2,3-dimethoxy-4-hydroxy-1-n-propanoyloxynaphthalene;
6-methyl-2,3-dimethoxy-4-hydroxy-1-i-buanoyloxynaphthalene;
6-methyl-2,3-dimethoxy-4-hydroxy-1-(2,2-dimethylpropanoyloxy)naphthalene;
6,7-dimethyl-2,3-dimethoxy-4-hydroxy-1-acetyloxynaphthalene;
6,7-dimethyl-2,3-dimethoxy-4-hydroxy-1-n-propanoyloxynaphthalene;
6,7-dimethyl-2,3-dimethoxy-4-hydroxy-1-n-butanoyloxynaphthalene;
6,7-dimethyl-2,3-dimethoxy-4-hydroxy-1-i-butanoyloxynaphthalene;
6,7-dimethyl-2,3-dimethoxy-4-hydroxy-1-(2,2-dimethylpropanyloxy)naphthalene;
2,3-dimethoxy-4-hydroxy-1-benzoyloxynaphthalene;
6-chloro-2,3-dimethoxy-4-hydroxy-1-benzoyloxynaphthalene;
6-chloro-2,3-diethoxy-4-hydroxy-1-(2-chlorobenzoyloxy)naphthalene;
6-chloro-2,3-diethoxy-4-hydroxy-1-(3-bromobenzoyloxy)naphthalene;
6-chloro-2,3-di-n-propoxy-4-hydroxy-1-(4-ethylbenzoyloxy)naphthalene;
6-chloro-2,3-di-n-propoxy-4-hydroxy-1-(4-fluorobenzoyloxy)naphthalene;
6-chloro-2,3-diethoxy-4-hydroxy-1-(2-methoxybenzoyloxy)naphthalene;
6-chloro-2,3-diethoxy-4-hydroxy-1-(4-ethoxybenzoyloxy)naphthalene;
6-chloro-2,3-di-n-butyloxy-4-hydroxy-1-(2-hydroxy-4-chlorobenzoyloxy)naphthalene;
6-chloro-2,3-di-n-butyloxy-4-hydroxy-1-(3,5-dichlorobenzoyloxy)naphthalene;
6-chloro-2,3-dimethoxy-4-hydroxy-1-(2,6-dimethylbenzoyloxy)napthalene;
2,3-dimethoxy-4-hydroxy-1-phenylacetyloxynaphthalene; 6-chloro-2,3-dimethoxy-4-hydroxy-1-phenylacetyloxynaphthalene;
6-chloro-2,3-diethoxy-4-hydroxy-1-(2-chlorophenylacetyloxynaphthalene;
6-chloro-2,3-diethoxy-4-hydroxy-1-(4-fluorophenylacetyloxynaphthalene;
6-chloro-2,3-di-n-propoxy-4-hydroxy-1-(2-methoxyphenylacetyloxy)naphthalene;
6-chloro-2,3-di-n-propoxy-4-hydroxy-1-(4-methoxyphenylacetyloxy)naphthalene;
6-chloro-2,3-di-n-propoxy-4-hydroxy-1-(4-ethoxyphenylacetyloxy)naphthalene;
6-chloro-2,3-dimethoxy-4-hydroxy-1-(2-methylphenylacetyloxy)naphthalene;
6-chloro-2,3-dimethoxy-4-hydroxy-1-(4-ethylphenylacetyloxy)naphthalene;
2,3-diphenoxy-4-hydroxy-1-acetyloxynaphthalene;
6-chloro-2,3-diphenoxy-4-hydroxy-1-acetyloxynaphthalene;
6-chloro-2,3-di(2-chlorophenoxy)-4-hydroxy-1-benzoyloxynaphthalene;
6-chloro-2,3-di(2-chlorophenoxy)-4-hydroxy-1-(4-benzoyloxy)naphthalene;
6-chloro-2,3-diphenoxy-4-hydroxy-1-n-propanoyloxynaphthalene;
6-chloro-2,3-diphenoxy-4-hydroxy-1-n-butanoyloxynaphthalene;
6-chloro-2,3-di(4-chlorophenoxy)-4-hydroxy-1-4-benzoyloxynaphthalene;
6-chloro-2,3-di(4-methoxyphenoxy)-4-hydroxy-1-phenylacetyloxynaphthalene;
6-chloro-2,3-di(2-hydroxy-4-chlorophenoxy)-4-hydroxy-1-phenylacaetyloxynaphthalene;
6-chloro-2,3-di(3-methylphenoxy)-4-hydroxy-1-acetyloxynaphthalene;
6-chloro-2,3-di(4-ethylphenoxy)-4-hydroxy-1-benzyloxynaphthalene;
6-chloro-2,3-di(2-fluorophenoxy)-4-hydroxy-1-(2-methylbenzoyloxy)naphthalene;
2,3-diethoxy-4-hydroxy-1-acetyloxynaphthalene;
2,3-dimethoxy-4-hydroxy-1-propanoyloxynaphthalene;
2,3-dimethoxy-5-(imidazol-2-ylsulfinyl)-4-hydroxy-1-acetyloxynaphthalene;
2,3-dimethoxy-6-(2-chlorophenylsulfinyl)-4-hydroxy-1-acetyloxynaphthalene;
2,3-dimethoxy-5-(3-chlorophenylsulfinyl)-4-hydroxy-1-acetyloxynaphthalene;
2,3-dimethoxy-6-(4-chlorophenylsulfinyl)-4-hydroxy-1-acetyloxynaphthalene;
2,3-dimethoxy-5-(2,6-dichlorophenylsulfinyl)-4-hydroxy-1-acetyloxynaphthalene;
2,3-dimethoxy-5-(4-fluorophenylsulfinyl)-4-hydroxy-1-acetyloxynaphthalene;
2,3-dimethoxy-5-(2-bromophenylsulfinyl)-4-hydroxy-1-acetyloxynaphthalene;
2,3-dimethoxy-5-(4-bromophenylsulfinyl)-4-hydroxy-1-acetyloxynaphthalene;
2,3-diethoxy-6-(4-methoxyphenylsulfinyl)-4-hydroxy-1-acetyloxynaphthalene;
2,3-dipropoxy-6-(4-nitrophenylsulfinyl)-4-hydroxy-1-acetyloxynaphthalene;
2,3-di-n-butoxy-6-(2-ethylphenylsulfinyl)-4-hydroxy-1-acetyloxynaphthalene;
2,3-dimethoxy-6-(pyrimidin-2-ylsulfinyl)-4-hydroxy-1-acetyloxynaphthalene;
2,3-dimethoxy-5-(pyrimidin-4-ylsulfinyl)-4-hydroxy-1-acetyloxynaphthalene;
2,3-dimethoxy-6-methylsulfinyl-4-hydroxy-1-acetyloxynaphthalene;
2,3-dimethoxy-5-benzylsulfinyl-4-hydroxy-1-acetyloxynaphthalene; and
2,3-dimethoxy-5-methoxycarbonylmethylsulfinyl-4-hydroxy-1-acetyloxynaphthalene.

E. Similarly, proceeding as in Example 1, but not separating the isomers the following compound, for example, is prepared:
6-chloro-2,3-dimethoxy-1-hydroxy-4-(2,2-dimethylpropanoyloxy)napthalene and its regioisomer, 98°–99° C.

EXAMPLE 2

(Preparation of a compound of formula (Ib))

A. A solution of 6-chloro-2,3-dimethoxy-1-hydroxy-4-(2,2-dimethylpropanoyloxy)naphthalene and 6-chloro-2,3-dimethoxy-4-hydroxy-1-(2,2-dimethylpropanoyloxy)naphthalene (2.80 g) in tetrahydrofuran was treated with a tetrahydrofuran solution containing acetic anhyride (1.27 g) pyridine (1.0 ml) and dimethylaminopyridine (0.1 g) at room temperature. After stirring overnight, the mixture was concentrated, and the residue was dissolved in ether. The organic layer was washed with 1M HCl and brine, then dried, filtered and evaporated. The residue was crystallized from ether/pentane to give an isomeric mixture of 6-chloro-2,3-dimethoxy-1-acetyloxy-4-(2,2-dimethylpropanoyloxynaphthalene, and 6-chloro-2,3-dimethoxy-4-acetyloxy-1-(2,2-dimethylpropanoyloxy)naphthalene, m.p. 86°–87° C.

B. Similarly, using the compounds from Part C of Example 1 the following compounds, for example, are prepared:

6-chloro-2,3-dimethoxy-1-acetyloxy-4-n-propanoyloxynaphthalene;
6-chloro-2,3-dimethoxy-1-propanoyloxy-4-i-butanoyloxynaphthalene;
6-chloro-2,3-dimethoxy-1-n-butanoyloxy-4-(2,2-dimethylpropanoyloxy)naphthalene;
6-chloro-2,3-dimethoxy-1-i-butanoyloxy-4-n-octanoyloxynaphthalene;
6-chloro-2,3-di-n-butoxy-1-n-pentanoyloxy-4-acetyloxynaphthalene;
6-chloro-2,3-di-s-butoxy-1-i-pentanoyloxy-4-acetyloxynaphthalene;
6-chloro-2,3-di(2,2-dimethylpropoxy)-1-(2-methylbutanoyloxy)-4-acetyloxynaphthalene;
2,3-di-n-butoxy-1-(2,2-dimethylpropanoyloxy)-4-n-pentanoyloxynaphthalene;
6-chloro-2,3-di-n-propoxy-1-n-hexanoyloxy-4-propanoyloxynaphthalene;
6-chloro-2,3-di-i-propoxy-1-(2,2-dimethylbutanoyloxy)-4-octanoyloxynaphthalene;
6-bromo-2,3-dimethoxy-1-(3,3-dimethylbutanoyloxy)-4-acetyloxynaphthalene;
6-fluoro-2,3-dimethoxy-1-n-heptanoyloxy-4-acetyloxynaphthalene;
5-chloro-2,3-dimethoxy-1-(2,2-dimethylpentanoyloxy)-4-acetyloxynaphthalene;
5-cyano-2,3-dimethoxy-1-(3,3-dimethylpentanoyloxy)-4-acetyloxynaphthalene;
6-cyano-2,3-dimethoxy-1-n-octanoyloxy-4-acetyloxynaphthalene;
6-methylamino-2,3-dimethoxy-1-(2,2-dimethylhexanoyloxy)-4-acetyloxynaphthalene;
6-diethylamino-2,3-dimethoxy-1-(3,3-dimethylhexanoyloxy)-4-propanoyloxynaphthalene;
6-ethylmethylamino-2,3-dimethoxy-1-benzoyloxy-4-n-butanoyloxynaphthalene;
2,3,6-trimethoxy-1-(2-chlorobenzoyloxy)-4-n-pentanoyloxynaphthalene;
2,3,6-triethoxy-1-(3-bromobenzoyloxy)-4-n-hexanoyloxynaphthalene;
6-i-butoxy-2,3-dimethoxy-1-(4-ethylbenzoyloxy)-4-(2,2-dimethylpropanoyloxy)naphthalene;
6-phenylethoxy-2,3-dimethoxy-1-(4-fluorobenzoyloxy)-4-acetyloxynaphthalene;
6-methyl-2,3-dimethoxy-1-(2-methoxybenzoyloxy)-4-acetyloxynaphthalene;
6-i-propyl-2,3-dimethoxy-1-phenylacetyloxy-4-n-octanoyloxynaphthalene;
6-phenyl-2,3-dimethoxy-1-(4-chlorophenylacetyloxy)-4-acetyloxynaphthalene;
6-benzyl-2,3-dimethoxy-1-acetyloxy-4-propanoyloxynaphthalene;
5-chloro-2,3-di-n-pentyloxy-1-propanoyloxy-4-n-butanoyloxynaphthalene;
5-chloro-2,3-di-s-pentyloxy-1-n-butanoyloxy-4-acetyloxynaphthalene;
5-chloro-2,3-di-n-hexyloxy-1-i-butanoyloxy-4-n-octanoyloxynaphthalene;
5-chloro-2,3-di-i-hexyloxy-1-n-pentanoyloxy-4-acetyloxynaphthalene;
5-chloro-2,3-dimethoxy-1-i-pentanoyloxy-4-(2,2-dimethylpropanoyloxynaphthalene;
6-chloro-2,3-dimethoxy-1-(2-methylbutanoyloxy)-4-n-butanoyloxynaphthalene;
6-chloro-2,3-diethoxy-1-(2,2-dimethylpropanoyloxy)-4-acetyloxynaphthalene;
6-chloro-2,3-diethoxy-1-n-hexanoyloxy-4-n-propanoyloxynaphthalene;
6-chloro-2,3-diethoxy-1-(2,2-dimethylbutanoyloxy)-4-i-butanoyloxynaphthalene;
6-chloro-2,3-diethoxy-1-(3,3-dimethylbutanoyloxy)-4-(2,2-dimethylpropanoyloxy)naphthalene;
6-chloro-2,3-di-n-propoxy-1-n-heptanoyloxy-4-i-butanoyloxynaphthalene;
6-chloro-2,3-di-n-propoxy-1-(2,2-dimethylpentanoyloxy)-4-(2,2-dimethylpropanoyloxy)naphthalene;
2,3,5-trimethoxy-1-(3,3-dimethylpentanoyloxy)-4-acetyloxynaphthalene;
2,3,5-trimethoxy-1-n-octanoyloxy-4-n-propanoyloxynaphthalene;
2,3,5-trimethoxy-1-(2,2-dimethylhexanoyloxy)-4-(2,2-dimethylpropanoyloxy)naphthalene;
2,3,6-trimethoxy-1-(3,3-dimethylhexanoyloxy)-4-n-propanoyloxynaphthalene;
2,3,6-trimethoxy-1-benzoyloxy-4-(2,2-dimethylpropanoyloxy)naphthalene;
6-chloro-2,3-di-n-propoxy-1-(2-chlorobenzoyloxy)-4-acetyloxynaphthalene;
6-chloro-2,3-di-i-propoxy-1-(3-bromobenzoyloxy)-4-acetyloxynaphthalene;
6-chloro-2,3-di-i-propoxy-1-(4-ethylbenzoyloxy)-4-n-butanoyloxynaphthalene, oil;
6-chloro-2,3-di-i-propoxy-1-(4-fluorobenzoyloxy)-4-i-butanoyloxynaphthalene;
6-chloro-2,3-di-i-propoxy-1-(2-methoxybenzoyloxy)-4-(2,2-dimethylpropanoyloxy)naphthalene;
2,3,6-trimethoxy-1-(2,4-dichlorobenzoyloxy)-4-acetyloxynaphthalene;
5-methyl-2,3-dimethoxy-1-phenylacetyloxy-4-acetyloxynaphthalene;
5-methyl-2,3-dimethoxy-1-(4-chlorophenylacetyloxy)-4-n-propanoyloxynaphthalene;
5-methyl-2,3-dimethoxy-1-acetyloxy-4-i-butanoyloxynapthalene;
5-methyl-2,3-dimethoxy-1-propanoyloxy-4-(2,2-dimethylpropanoyloxy)naphthalene;
6-methyl-2,3-dimethoxy-1-n-butanoyloxy-4-n-propanoyloxynaphthalene;
6-methyl-2,3-dimethoxy-1-i-butanoyloxy-4-i-butanoyloxynaphthalene, oil;
6-methyl-2,3-dimethoxy-1-n-pentanoyloxy-4-(2,2-dimethylpropanoyloxy)naphthalene;
6,7-dimethyl-2,3-dimethoxy-1-i-pentanoyloxy-4-acetyloxynaphthalene;
6,7-dimethyl-2,3-dimethoxy-1-(2-methylbutanoyloxy)-4-n-propanoyloxynaphthalene;
6,7-dimethyl-2,3-dimethoxy-1-(2,2-dimethylpropanoyloxy)-4-n-butanoyloxynaphthalene;
6,7-dimethyl-2,3-dimethoxy-1-n-hexanoyloxy-4-i-butanoyloxynaphthalene;

6,7-dimethyl-2,3-dimethoxy-1-(2,2-dimethylbutanoyloxy)-4-(2,2-dimethylpropanyloxy)naphthalene;
2,3-dimethoxy-1-(3,3-dimethylbutanoyloxy)-4-benzoyloxynaphthalene;
6-chloro-2,3-dimethoxy-1-n-heptanoyloxy-4-benzoyloxynaphthalene;
6-chloro-2,3-diethoxy-1-(2,2-dimethylpentanoyloxy)-4-(2-chlorobenzoyloxy)naphthalene;
6-chloro-2,3-diethoxy-1-(3,3-dimethylpentanoyloxy)-4-(3-bromobenzoyloxy)naphthalene;
6-chloro-2,3-di-n-propoxy-1-n-octanoyloxy-4-(4-ethylbenzoyl-oxy)naphthalene;
6-chloro-2,3-di-n-propoxy-1-(2,2-dimethylhexanoyloxy)-4-(4-fluorobenzoyloxy)naphthalene;
6-chloro-2,3-diethoxy-1-(3,3-dimethylhexanoyloxy)-4-(2-methoxybenzoyloxy)naphthalene;
6-chloro-2,3-diethoxy-1-benzoyloxy-4-(4-ethoxybenzoyloxy)naphthalene;
6-chloro-2,3-di-n-butyloxy-1-(2-chlorobenzoyloxy)-4-(2-hydroxy-4-chlorobenzoyloxy)naphthalene;
6-chloro-2,3-di-n-butyloxy-1-(3-bromobenzoyloxy)-4-(3,5-dichlorobenzoyloxy)naphthalene;
6-chloro-2,3-dimethoxy-1-(4-ethylbenzoyloxy)-4-(2,6-dimethylbenzoyloxy)naphthalene;
2,3-dimethoxy-1-(4-fluorobenzoyloxy)-4-phenylacetyloxynaphthalene;
6-chloro-2,3-dimethoxy-1-(2-methoxybenzoyloxy)-4-phenylacetyloxynaphthalene;
6-chloro-2,3-diethoxy-1-(2,4-dichlorobenzoyloxy)-4-(2-chlorophenylacetyloxynaphthalene;
6-chloro-2,3-diethoxy-1-phenylacetyloxy-4-(4-fluorophenylacetyloxy)naphthalene;
6-chloro-2,3-di-n-propoxy-1-(4-chlorophenylacetyloxy)-4-(2-methoxyphenylacetyloxy)naphthalene;
6-chloro-2,3-di-n-propoxy-1-acetyloxy-4-(4-methoxyphenylacetyloxy)naphthalene;
6-chloro-2,3-di-n-propoxy-1-propanoyloxy-4-(4-ethoxyphenyl-acetyloxy)naphthalene;
6-chloro-2,3-dimethoxy-1-n-butanoyloxy-4-(2-methylphenylacetyloxy)naphthalene;
6-chloro-2,3-dimethoxy-1-i-butanoyloxy-4-(4-ethylphenylacetyloxy)naphthalene;
2,3-diphenoxy-1-n-pentanoyloxy-4-acetyloxynaphthalene;
6-chloro-2,3-diphenoxy-1-i-pentanoyloxy-4-acetoyloxynaphthalene;
6-chloro-2,3-di(2-chlorophenoxy)-1-(2-methylbutanoyloxy)-4-benzoyloxynaphthalene;
6-chloro-2,3-di(2-chlorophenoxy)-1-(2,2-dimethylpropanoyloxy)-4-benzoyloxynaphthalene;
6-chloro-2,3-diphenoxy-1-n-hexanoyloxy-4-n-propanoyloxynaphthalene;
6-chloro-2,3-diphenoxy-1-(2,2-dimethylbutanoyloxy)-4-n-butanoyloxynaphthalene;
6-chloro-2,3-di(4-chlorophenoxy)-1-(3,3-dimethylbutanoyloxy)-4-benzoyloxynaphthalene;
6-chloro-2,3-di(4-methoxyphenoxy)-1-n-heptanoyloxy-4-phenylacetyloxynaphthalene;
6-chloro-2,3-di(2-chlorophenoxy)-1-(2,2-dimethylpentanoyloxy)-4-phenylacetyloxynaphthalene;
6-chloro-2,3-di(3-methylphenoxy)-1-(2,2-dimethylpentanoyloxy)-4-acetyloxynaphthalene;
6-chloro-2,3-di(4-ethylphenoxy)-1-(3,3-dimethylpentanoyloxy)-4-benzyloxynaphthalene;
6-chloro-2,3-di(2-fluorophenoxy)-1-n-octanoyloxy-4-(2-methylbenzoyloxy)naphthalene;
2,3-dimethoxy-1-acetyloxy-4-(2,2-dimethylpropanoyloxy)naphthalene;
2,3-diethoxy-1-acetyloxy-4-(2,2-dimethylpropanoyloxy)naphthalene;
2,3-dimethoxy-1-acetyloxy-4-propanoyloxynaphthalene;
2,3-dimethoxy-5-(imidazol-2-ylsulfinyl)-1-(2,2-dimethylhexanoyloxy)-4-acetyloxynaphthalene;
2,3-dimethoxy-6-(2-chlorophenylsulfinyl)-1-(3,3-dimethylhexanoyloxy)-4-acetyloxynaphthalene;
2,3-dimethoxy-5-(3-chlorophenylsulfinyl)-1-benzoyloxy-4-acetyloxynaphthalene;
2,3-dimethoxy-6-(4-chlorophenylsulfinyl)-1-(2-chlorobenzoyloxy)-4-acetyloxynaphthalene;
2,3-dimethoxy-5-(2,6-dichlorophenylsulfinyl)-1-(3-bromobenzoyloxy)-4-acetyloxynaphthalene;
2,3-dimethoxy-5-(4-fluorophenylsulfinyl)-1-(4-ethylbenzoyloxy)-4-acetyloxynaphthalene;
2,3-dimethoxy-5-(2-bromophenylsulfinyl)-1-(4-fluorobenzoyloxy)-4-acetyloxynaphthalene;
2,3-dimethoxy-5-(4-bromophenylsulfinyl)-1-(2-methoxybenzoyloxy)-4-acetyloxynaphthalene;
2,3-diethoxy-6-(4-methoxyphenylsulfinyl)-1-(2,4-dichlorobenzoyloxy)-4-acetyloxynaphthalene;
2,3-dipropoxy-6-(4-nitrophenylsulfinyl)-1-phenylacetyloxy-4-acetyloxynaphthalene;
2,3-di-n-butoxy-6-(2-ethylphenylsulfinyl)-1-(4-chlorophenylacetyloxy)-4-acetyloxynaphthalene;
2,3-dimethoxy-6-(pyrimidin-2-ylsulfinyl)-1-(2-ethylphenylacetyloxy)-4-acetyloxynaphthalene;
2,3-dimethoxy-5-(pyrimidin-4-ylsulfinyl)-1-propanoyloxy-4-acetyloxynaphthalene;
2,3-dimethoxy-6-methylsulfinyl-1-n-butanoyloxy-4-acetyloxynaphthalene;
2,3-dimethoxy-5-benzylsulfinyl-1-i-butanoyloxy-4-acetyloxynaphthalene; and
2,3-dimethoxy-5-methoxycarbonylmethylsulfinyl-1-n-pentanoyloxy-4-acetyloxynaphthalene.

C. Similarly, using the compounds in Part B of Example 1 above, the following compounds, for example, are prepared:
6-chloro-2,3-dimethoxy-4-acetyloxy-1-n-porpanoyloxynaphthalene;
6-chloro-2,3-dimethoxy-4-propanoyloxy-1-i-butanoyloxynaphthalene;
6-chloro-2,3-dimethoxy-4-n-butanoyloxy-1-(2,2-dimethylpropanoyloxy)naphthalene;
6-chloro-2,3-dimethoxy-4-i-butanoyloxy-1-n-octanoyloxynaphthalene;
6-chloro-2,3-di-n-butoxy-4-n-pentanoyloxy-1-acetyloxynaphthalene;
6-chloro-2,3-di-s-butoxy-4-i-pentanoyloxy-1-acetyloxynaphthalene;
6-chloro-2,3-di(2,2-dimethylpropoxy)-4-(2-methylbutanoyloxy)-1-acetyloxynaphthalene;
2,3-di-n-butoxy-4-(2,2-dimethylpropanoyloxy)-1-n-pentoyloxynaphthalene;
6-chloro-2,3-di-n-propoxy-4-n-hexanoyloxy-1-propanoyloxynaphthalene;
6-chloro-2,3-di-i-propoxy-4-(2,2-dimethylbutanoyloxy)-1-octanoyloxynaphthalene;
6-bromo-2,3-dimethoxy-4-(3,3-dimethylbutanoyloxy)-1-acetyloxynaphthalene;
6-fluoro-2,3-dimethoxy-4-n-heptanoyloxy-1-acetyloxynaphthalene;
5-chloro-2,3-dimethoxy-4-(2,2-dimethylpentanoyloxy)-1-acetyloxynaphthalene;

5-cyano-2,3-dimethoxy-4-(3,3-dimethylpentanoyloxy)-1-acetyloxynaphthalene;
6-cyano-2,3-dimethoxy-4-n-octanoyloxy-1-acetyloxynaphthalene;
6-methylamino-2,3-dimethoxy-4-(2,2-dimethylhexanoyloxy)-1-acetyloxynaphthalene;
6-diethylamino-2,3-dimethoxy-4-(3,3-dimethylhexanoyloxy)-1-propanoyloxynaphthalene;
6-ethylmethylamino-2,3-dimethoxy-4-benzoyloxy-1-n-butanoyloxynaphthalene;
2,3,6-trimethoxy-4-(2-chlorobenzoyloxy)-1-n-pentanoyloxynaphthalene;
2,3,6-triethoxy-4-(3-bromobenzoyloxy)-1-n-hexanoyloxynaphthalene;
6-i-butoxy-2,3-dimethoxy-4-(1-ethylbenzoyloxy)-1-(2,2-dimethylpropanoyloxy)naphthalene;
6-phenylethoxy-2,3-dimethoxy-4-(1-fluorobenzoyloxy)-1-acetyloxynaphthalene;
6-methyl-2,3-dimethoxy-4-(2-methoxybenzoyloxy)-1-acetyloxynaphthalene;
6-i-propyl-2,3-dimethoxy-4-phenylacetyloxy-1-n-octanoyloxynaphthalene;
6-phenyl-2,3-dimethoxy-4-(1-chlorophenylacetyloxy)-1-acetyloxynaphthalene;
6-benzyl-2,3-dimethoxy-4-acetyloxy-1-propanoyloxynaphthalene;
5-chloro-2,3-di-n-pentyloxy-4-propanoyloxy-1-n-butanoyloxynaphthalene;
5-chloro, 2,3-di-s-pentyloxy-4-n-butanoyloxy-1-acetyloxynaphthalene;
5-chloro-2,3-di-n-hexyloxy-4-i-butanoyloxy-1-n-octanoyloxynaphthalene;
5-chloro-2,3-di-i-hexyloxy-4-n-pentanoyloxy-1-acetyloxynaphthalene;
5-chloro-2,3-dimethoxy-4-i-pentanoyloxy-1-(2,2-dimethylpropanoyloxynaphthalene;
6-chloro-2,3-dimethoxy-4-(2-methylbutanoyloxy)-1-n-butanoyloxynaphthalene;
6-chloro-2,3-diethoxy-4-(2,2-dimethylpropanoyloxy)-1-acetyloxynaphthalene;
6-chloro-2,3-diethoxy-4-n-hexanoyloxy-1-n-propanoyloxynaphthalene;
6-chloro-2,3-diethoxy-4-(2,2-dimethylbutanoyloxy)-1-i-butanoyloxynaphthalene;
6-chloro-2,3-diethoxy-4-(3,3-dimethylbutanoyloxy)-1-(2,2-dimethylpropanoyloxy)naphthalene;
6-chloro-2,3-di-n-propoxy-4-n-heptanoyloxy-1-i-butanoyloxynaphthalene;
6-chloro-2,3-di-n-propoxy-4-(2,2-dimethylpentanoyloxy)-1-(2,2-dimethylpropanoyloxy)naphthalene;
2,3,5-trimethoxy-4-(3,3-dimethylpentanoyloxy)-1-acetyloxynaphthalene;
2,3,5-trimethoxy-4-n-octanoyloxy-1-n-propanoyloxynaphthalene;
2,3,5-trimethoxy-4-(2,2-dimethylhexanoyloxy)-1-(2,2-dimethylpropanoyloxy)naphthalene;
2,3,6-trimethoxy-4-(3,3-dimethylhexanoyloxy)-1-n-propanoyloxynaphthalene;
2,3,6-trimethoxy-4-benzoyloxy-1-(2,2-dimethylpropanoyloxy)naphthalene;
6-chloro-2,3-di-n-propoxy-4-(2-chlorobenzoyloxy)-1-acetyloxynaphthalene;
6-chloro-2,3-di-i-propoxy-4-(3-bromobenzoyloxy)-1-acetyloxynaphthalene;
6-chloro-2,3di-i-propoxy-4-(1-ethylbenzoyloxy)-1-n-butanoyloxynaphthalene;
6-chloro-2,3-di-i-propoxy-4-(1-fluorobenzoyloxy)-1-i-butanoyloxynaphthalene;
6-chloro-2,3-di-i-propoxy-4-(2-methoxybenzoyloxy)-1-(2,2-dimethylpropanoyloxy)naphthalene;
2,3,6-trimethoxy-4-(2,1-dichlorobenzoyloxy)-1-acetyloxynaphthalene;
5-methyl-2,3-dimethoxy-4-phenylacetyloxy-1-acetyloxynaphthalene;
5-methyl-2,3-dimethoxy-4-(1-chlorophenylacetyloxy)-1-n-propanoyloxynaphthalene;
5-methyl-2,3-dimethoxy-4-acetyloxy-1-i-butanoyloxynaphthalene;
5-methyl-2,3-dimethoxy-4-propanoyloxy-1-(2,2-dimethylpropanoyloxy)naphthalene;
6-methyl-2,3-dimethoxy-4-n-butanoyloxy-1-n-propanoyloxynaphthalene;
6-methyl-2,3-dimethoxy-4-n-pentanoyloxy-1-(2,2-dimethylpropanoyloxy)naphthalene;
6,7-dimethyl-2,3-dimethoxy-4-i-pentanoyloxy-1-acetyloxynaphthalene;
6,7-dimethyl-2,3-dimethoxy-4-(2-methylbutanoyloxy)-4-n-propanoyloxynaphthalene;
6,7-dimethyl-2,3-dimethoxy-4-(2,2-dimethylpropanoyloxy)-1-n-butanoyloxynaphthalene;
6,7-dimethyl-2,3-dimethoxy-4-n-hexanoyloxy-1-i-butanoyloxynaphthalene;
6,7-dimethyl-2,3-dimethoxy-4-(2,2-dimethylbutanoyloxy)-1-(2,2-dimethylpropanyloxy)naphthalene;
2,3-dimethoxy-4-(3,3-dimethylbutanoyloxy)-1-benzoyloxynaphthalene;
6-chloro-2,3-dimethoxy-4-n-heptanoyloxy-1-benzoyloxynaphthalene;
6-chloro-2,3-diethoxy-4-(2,2-dimethylpentanoyloxy)-1-(2-chlorobenzoyloxy)naphthalene;
6-chloro-2,3-diethoxy-4-(3,3-dimethylpentanoyloxy)-1-(3-bromobenzoyloxy)naphthalene;
6-chloro-2,3-di-n-propoxy-4-n-octanoyloxy-1-(4-ethylbenzoyl-oxy)naphthalene;
6-chloro-2,3-di-n-propoxy-4-(2,2-dimethylhexanoyloxy)-1-(1-fuorobenzoyloxy)naphthalene;
6-chloro-2,3-diethoxy-4-(3,3-dimethylhexanoyloxy)-1-(2-methoxybenzoyloxy)naphthalene;
6-chloro-2,3-diethoxy-4-benzoyloxy-1-(1-ethoxybenzoyloxy)naphthalene;
6-chloro-2,3-di-n-butyloxy-4-(2-chlorobenzoyloxy)-1-(2-hydroxy-1-chlorobenzoyloxy)naphthalene;
6-chloro-2,3-di-n-butyloxy-4-(3-bromobenzoyloxy)-1-(3,5-dichlorobenzoyloxy)naphthalene;
6-chloro-2,3-dimethoxy-4-(1-ethylbenzoyloxy)-1-(2,6-dimethylbenzoyloxy)naphthalene;
2,3-dimethoxy-4-(1-fluorobenzoyloxy)-1-phenylacetyloxynaphthalene;
6-chloro-2,3-dimethoxy-4-(2-methoxybenzoyloxy)- 1-phenylacetyloxynaphthalene;
6-chloro-2,3-diethoxy-4-(2,1-dichlorobenzoyloxy)-1-(2-chlorophenylacetyloxynaphthalene;
6-chloro-2,3-diethoxy-4-phenylacetyloxy-1-(1-fluorophenylacetyloxynaphthalene;
6-chloro-2,3-di-n-propoxy-4-(1-chlorophenylacetyloxy)-1-(2-methoxyphenylacetyloxy)naphthalene;
6-chloro-2,3-di-n-propoxy-4-acetyloxy-1-(1-methoxyphenylacetyloxy)naphthalene;
6-chloro-2,3-di-n-propoxy-4-propanoyloxy-1-(1-ethoxyphenyl-acetyloxy)naphthalene;
6-chloro-2,3-dimethoxy-4-n-butanoyloxy-1-(2-methylphenylacetyloxy)naphthalene;
6-chloro-2,3-dimethoxy-4-i-butanoyloxy-1-(1-ethylphenylacetyloxy)naphthalene;

2,3-diphenoxy-4-n-pentanoyloxy-1-acetyloxynaphthalene;
6-chloro-2,3-diphenoxy-4-i-pentanoyloxy-1-acetoyloxynaphthalene;
6-chloro-2,3-di(2-chlorophenoxy)-4-(2-methylbutanoyloxy)-1-benzoyloxynaphthalene;
6-chloro-2,3-di(2-chlorophenoxy)-4-(2,2-dimethylpropanoyloxy)-1-benzoyloxynaphthalene;
6-chloro-2,3-diphenoxy-4-n-hexanoyloxy-1-n-propanoyloxynaphthalene;
6-chloro-2,3-diphenoxy-4-(2,2-dimethylbutanoyloxy)-1-n-butanoyloxynaphthalene;
6-chloro-2,3-di(1-chlorophenoxy)-4-(3,3-dimethylbutanoyloxy)-1-benzoyloxynaphthalene;
6-chloro-2,3-di(1-methoxyphenoxy)-4-n-heptanoyloxy-1-phenylacetyloxynaphthalene;
6-chloro-2,3di-(2-chlorophenoxy)-4-(2,2-dimethylpentanoyloxy)-1-phenylacetyloxynaphthalene;
6-chloro-2,3-di(3-methylphenoxy)-4-(2,2-dimethylpentanoyloxy)-1-acetyloxynaphthalene;
6-chloro-2,3-di(1-ethylphenoxy)-4-(3,3-dimethylpentanoyloxy)-1-benzoyloxynaphthalene;
6-chloro-2,3-di(2-fluorophenoxy)-4-n-octanoyloxy-1-(2-methylbenzoyloxy)naphthalene;
2,3-dimethoxy-4-acetyloxy-1-(2,2-dimethylpropanoyloxy)naphthalene;
2,3-diethoxy-4-acetyloxy-1-(2,2-dimethylpropanoyloxy)naphthalene;
2,3-dimethoxy-4-acetyloxy-1-propanoyloxynaphthalene;
2,3-dimethoxy-5-(imidazol-2-ylsulfinyl)-4-(2,2-dimethylhexanoyloxy)-1-acetyloxynaphthalene;
2,3-dimethoxy-6-(2-chlorophenylsulfinyl)-4-(3,3-dimethylhexanoyloxy)-1-acetyloxynaphthalene;
2,3-dimethoxy-5-(3-chlorophenylsulfinyl)-4-benzoyloxy-1-acetyloxynaphthalene;
2,3-dimethoxy-6-(1-chlorophenylsulfinyl)-4-(2-chlorobenzoyloxy)-1-acetyloxynaphthalene;
2,3-dimethoxy-5-(2,6-dichlorophenylsulfinyl)-4-(3-bromobenzoyloxy)-1-acetyloxynaphthalene;
2,3-dimethoxy-5-(1-fluorophenylsulfinyl)-4-(1-ethylbenzoyloxy)-1-acetyloxynaphthalene;
2,3-dimethoxy-5-(2-bromophenylsulfinyl)-4-(1-fluorobenzoyloxy)-1-acetyloxynaphthalene;
2,3-dimethoxy-5-(1-bromophenylsulfinyl)-4-(2-methoxybenzoyloxy)-1-acetyloxynaphthalene;
2,3-diethoxy-6-(1-methoxyphenylsulfinyl)-4-(2,4-dichlorobenzoyloxy)-1-acetyloxynaphthalene;
2,3-diproproxy-6-(1-nitrophenylsulfinyl)-4-phenylacetyloxy-1-acetyloxynaphthalene;
2,3-di-n-butoxy-6-(2-ethylphenylsulfinyl)-4-(1-chlorophenylacetyloxy)-1-acetyloxynaphthalene;
2,3-dimethoxy-6-(pyrimidin-2-ylsulfinyl)-4-(2-ethylphenylacetyloxy)-1-acetyloxynaphthalene;
2,3-dimethoxy-5-(pyrimidin-1-ylsulfinyl)-4-propanoyloxy-1-acetyloxynaphthalene;
2,3-dimethoxy-6-methylsulfinyl-4-n-butanoyloxy-1-acetyloxynaphthalene;
2,3-dimethoxy-5-benzylsulfinyl-4-i-butanoyloxy-1-acetyloxynaphthalene; and
2,3-dimethoxy-5-methoxycarbonylmethylsulfinyl-4-n-pentanoyloxy-1-acetyloxynaphthalene.

EXAMPLE 3

(Preparation of a compound of formula (Ic)

A. Diazabicycloundecane (DBU,, 3.7 ml) is added to a solution of 2,3-dimethoxy-1-hydroxy-4-(2,2-dimethylpropanoyloxy)naphthalene (6.1 g) and benzyl bromide (2.6 ml). After heating at 60° C. for 2 hours, the reaction is cooled, and the resulting DBU hydrobromide is filtered off. The filtrate is evaporated, and then is dissolved in ethyl acetate. The organic layer is washed with 1M HCl and brine, then dried, filtered and evaporated to yield 2,3-dimethoxy-1-benzyloxy-4-(2,2-dimethylpropanoyloxy)naphthalene (7.3 g) as a syrup after chromatography over silica gel.

B. Similarly, using the compounds from Part C of Example I, the following compounds, for example, are prepared:
6-chloro-2,3-dimethoxy-1-ethoxy-4-i-butanoyloxynaphthalene;
6-chloro-2,3-dimethoxy-1-n-propoxy-4-(2,2-dimethylpropanoyl-oxy)naphthalene;
6-chloro-2,3-dimethoxy-1-i-propoxy-4-n-octanoyloxynaphthalene;
6-chloro-1,2,3-tri-n-butoxy-4-acetyloxynaphthalene;
6-chloro-2,3-di-s-butoxy-1-i-butoxy-4-acetyloxynaphthalene;
6-chloro-2,3-di(2,2-dimethylpropoxy)-1-s-butoxy-4-acetyloxy-naphthalene;
2,3-di-n-butoxy-1-n-pentyloxy-4-n-pentoyloxynaphthalene;
6-chloro-2,3-di-n-propoxy-1-s-penyloxy-4-propanoyloxynaphthalene;
6-chloro-2,3-di-i-propoxy-1-n-hexyloxy-4-octanoyloxynaphthalene;
6-bromo-2,3-dimethoxy-1-i-hexyloxy-4-acetyloxynaphthalene;
6-fluoro-2,3-dimethoxy-1-benzyloxy-4-acetyloxynaphthalene;
5-chloro-2,3-dimethoxy-1-(4-chlorobenzyloxy)-4-acetyloxynaphthalene;
5-cyano-2,3-dimethoxy-1-(4-methoxyphenylethoxy)-4-acetyloxynaphthalene;
6-cyano-2,3-dimethoxy-1-(2,4-dichlorophenyl-n-propoxy)-4-acetyloxynaphthalene;
6-methylamino-2,3-dimethoxy-1-(3-methylphenyl-n-butoxy)-4-acetyloxynaphthalene;
6-diethylamino-2,3-dimethoxy-1-(2-fluorophenyl-n-hexyloxy)-4-propanoyloxynaphthalene;
2,3,6-trimethoxy-1-ethoxy-4-n-pentanoyloxynaphthalene;
2,3,6-triethoxy-1-n-propoxy-4-n-hexanoyloxynaphthalene;
6-i-butoxy-2,3-dimethoxy-1-propoxy-4-(2,2-dimethylpropanoyloxy)naphthalene;
6-phenylethoxy-2,3-dimethoxy-1-n-butoxy-4-acetyloxynaphthalene;
6-methyl-2,3-dimethoxy-1-i-butoxy-4-acetyloxynaphthalene;
6-i-propyl-2,3-dimethoxy-1-s-butoxy-4-n-octanoyloxynaphthalene;
6-phenyl-2,3-dimethoxy-1-n-pentyloxy-4-acetyloxynaphthalene;
6-benzyl-2,3-dimethoxy-1-s-pentyloxy-4-propanoyloxynaphthalene;
5-chloro-2,3-di-n-pentyloxy-1-n-hexyloxy-4-n-butanoyloxy-naphthalene;
5-chloro-2,3-di-s-pentyloxy-1-i-hexyloxy-4-acetyloxynaphthalene;
5-chloro-2,3-di-n-hexyloxy-1-(3,5-dimethylbenzyloxy)-4-n-octanoyl-oxynaphthalene;
5-chloro-2,3-di-i-hexyloxy-1-(4-ethylphenylethoxy)-4-acetyloxynaphthalene;

5-chloro-2,3-dimethoxy-1-(2-propoxyphenyl-n-propoxy)-4-(2,2-dimethylpropanoyloxynaphthalene
6-chloro-2,3-dimethoxy-1-benzyloxy-4-n-butanoyloxynaphthalene;
6-chloro-2,3-diethoxy-1-(4-chlorobenzyloxy)-4-acetyloxy-naphthalene;
6-chloro-2,3-diethoxy-1-(4-methoxyphenylethoxy)-4-n-propanoyloxynaphthalene;
6-chloro-1,2,3-triethoxy-4-(2,2-dimethylpropanoyloxy)-naphthalene;
6-chloro-1,2,3-tri-n-propoxy-4-i-butanoyloxynaphthalene;
6-chloro-2,3-di-n-propoxy-1-i-propoxy-4-(2,2-dimethylpropanoyloxy)naphthalene;
2,3,5-trimethoxy-1-n-butoxy-4-acetyloxynaphthalene;
2,3,5-trimethoxy-1-i-butoxy-4-n-propanoyloxynaphthalene;
2,3,5-trimethoxy-1-s-butoxy-4-(2,2-dimethylpropanoyloxy)naphthalene;
2,3,5-trimethoxy-1-n-pentyloxy-4-n-propanoyloxynaphthalene;
2,3,6-trimethoxy-1-s-pentyloxy-4-(2,2-dimethylpropanoyloxy)naphthalene;
6-chloro-2,3-di-n-propoxy-1-n-hexyloxy-4-acetyloxynaphthalene;
6-chloro-2,3-di-i-propoxy-1-i-hexyloxy-4-acetyloxynaphthalene;
6-chloro-2,3-di-i-propoxy-1-benzyloxy-4-n-butanoyloxynaphthalene;
6-chloro-2,3-di-i-propoxy-1-(4-chlorobenzyloxy)-4-i-butanoyloxynaphthalene;
6-chloro-2,3-di-i-propoxy-1-(4-methoxyphenylethoxy)-4-(2,2-dimethylpropanoyloxy)naphthalene;
2,3,6-trimethoxy-1-(2,4-dichlorophenyl-n-propoxy)-4-acetyloxynaphthalene;
5-methyl-2,3-dimethoxy-1-(3-methylphenyl-n-butoxy)-4-acetyloxynaphthalene;
5-methyl-2,3-dimethoxy-1-(2-fluorophenyl-n-hexyloxy)-4-n-propanoyloxynaphthalene;
5-methyl-2,3-dimethoxy-1-ethoxy-4-(2,2-dimethylpropanoyloxy)naphthalene;
6-methyl-2,3-dimethoxy-1-n-propoxy-4-n-propanoyloxynaphthalene;
6-methyl-2,3-dimethoxy-1-i-propoxy-4-i-butanoyloxynaphthalene;
6-methyl-2,3-dimethoxy-1-n-butoxy-4-(2,2-dimethylpropanoyloxy)naphthalene;
6,7-dimethyl-2,3-dimethoxy-1-i-butoxy-4-acetyloxynaphthalene;
6,7-dimethyl-2,3-dimethoxy-1-s-butoxy-4-n-propanoyloxynaphthalene;
6,7-dimethyl-2,3-dimethoxy-1-n-pentyloxy-4-n-butanoyloxynaphthalene;
6,7-dimethyl-2,3-dimethoxy-1-s-pentyloxy-4-i-butanoyloxynaphthalene;
6,7-dimethyl-2,3-dimethoxy-1-n-hexyloxy-4-(2,2-dimethylpropanoyloxy)naphthalene;
2,3-dimethoxy-1-i-hexyloxy-4-benzoyloxynaphthalene;
6-chloro-2,3-dimethoxy-1-(3,5-dimethylbenzyloxy)-4-benzoyloxy-naphthalene;
6-chloro-2,3-diethoxy-1-(4-ethylphenylethoxy)-4-(2-chlorobenzoyloxy)naphthalene;
6-chloro-2,3-diethoxy-1-(2-propylphenyl-n-propoxy)-4-(3-bromobenzoyloxy)naphthalene;
6-chloro-2,3-di-n-propoxy-1-benzyloxy-4-(4-ethylbenzoyloxy)naphthalene;
6-chloro-2,3-di-n-propoxy-1-(4-chlorobenzyloxy)-4-(4-fluorobenzoyloxy)naphthalene;
6-chloro-2,3-diethoxy-1-(4-chlorophenylethoxy)-4-(2-methoxybenzoyloxy)naphthalene;
6-chloro-2,3-di-n-butoxy-1-ethoxy-4-(2-hydroxy-4-chlorobenzoyloxy)naphthalene;
6-chloro-2,3-di-n-butoxy-1-n-propoxy-4-(3,5-dichlorobenzoyloxy)naphthalene;
6-chloro-2,3-dimethoxy-1-i-propoxy-4-(2,6-dimethylbenzoyloxy)naphthalene;
2,3-dimethoxy-1-n-butoxy-4-phenylacetyloxynaphthalene;
6-chloro-2,3-dimethoxy-1-i-butoxy-4-phenylacetyloxynaphthalene;
6-chloro-2,3-diethoxy-1-s-butoxy-4-(2-chlorophenylacetyloxynaphthalene;
6-chloro-2,3-diethoxy-1-n-pentyloxy-4-(4-fluorophenylacetyloxynaphthalene;
6-chloro-2,3-di-n-propoxy-1-s-pentyloxy-4-(2-methoxyphenylacetyloxy)naphthalene;
6-chloro-2,3-di-n-propoxy-1-n-hexyloxy-4-(4-methoxyphenylacetyloxy)naphthalene;
6-chloro-2,3-di-n-propoxy-1-i-hexyloxy-4-(4-ethoxyphenylacetyloxy)naphthalene;
6-chloro-2,3-dimethoxy-1-(4-methylphenylethoxy)-4-(2-methylphenylacetyloxy)naphthalene;
6-chloro-2,3-dimethoxy-1-(4-chlorobenzyloxy)-4-(4-ethylphenylacetyloxy)naphthalene;
2,3-diphenoxy-1-(4-methoxyphenylethoxy)-4-acetyloxynaphthalene;
6-chloro-2,3-diphenoxy-1-(2,4-dichlorophenyl-n-propoxy)-4-acetyloxynaphthalene;
6-chloro-2,3-di(2-chlorophenoxy)-1-(3-methylphenyl)-n-butoxy)-4-benzoyloxynaphthalene;
6-chloro-2,3-di(2-chlorophenoxy)-1-(2-fluorophenyl-n-hexyloxy)-4-benzoyloxynaphthalene;
6-chloro-2,3-diphenoxy-1-(3,5-dimethylbenzyloxy)-4-n-propanoyloxynaphthalene;
6-chloro-2,3-di(4-chlorophenoxy)-1-ethoxy-4-benzoyloxynaphthalene;
6-chloro-2,3-di(4-methoxyphenoxy)-1-n-propoxy-4-phenylacetyloxynaphthalene;
6-chloro-2,3-di(2-hydroxy-4-chlorophenoxy)-1-i-propoxy-4-phenylacetyloxynaphthalene;
6-chloro-2,3-di(3-methylphenoxy)-1-n-butoxy-4-acetyloxynaphthalene;
6-chloro-2,3-di(4-ethylphenoxy)-1-i-butoxy-4-benzyloxynaphthalene;
6-chloro-2,3-di(2-fluorophenoxy)-1-s-butoxy-4-(2-methylbenzoyloxy)naphthalene;
2,3-dimethoxy-5-(imidazol-2-ylsulfinyl)-1-n-pentyloxy-4-acetyloxynaphthalene;
2,3-dimethoxy-6-(2-chlorophenylsulfinyl)-1-s-pentyloxy-4-acetyloxynaphthalene;
2,3-dimethoxy-5-(3-chlorophenylsulfinyl)-1-n-hexyloxy-4-acetyloxynaphthalene;
2,3-dimethoxy-6-(4-chlorophenylsulfinyl)-1-i-hexyloxy-4-acetyloxynaphthalene;
2,3-dimethoxy-5-(2,6-dichlorophenylsulfinyl)-1-benzyloxy-4-acetyloxynaphthalene;
2,3-dimethoxy-5-(4-fluorophenylsulfinyl)-1-(4-chlorobenzyloxy)-4-acetyloxynaphthalene;
2,3-dimethoxy-5-(2-bromophenylsulfinyl)-1-(4-methoxyphenylethoxy)-4-acetyloxynaphthalene;
2,3-dimethoxy-5-(4-bromophenylsulfinyl)-1-(2,4-dichlorophenyl-n-propoxy)-4-acetyloxynaphthalene;
2,3-diethoxy-6-(4-methoxyphenylsulfinyl)-1-(3-methylphenyl-n-butoxy)-4-acetyloxynaphthalene;
2,3-dipropoxy-6-(4-nitrophenylsulfinyl)-1-(2-fluorophenyl-n-hexyloxy)-4-acetyloxynaphthalene;

2,3-dimethoxy-6-(pyrimidin-2-ylsulfinyl)-1-ethoxy-4-acetyloxynaphthalene;
2,3-dimethoxy-5-(pyrimidin-4-ylsulfinyl)-1-n-propoxy-4-acetyloxynaphthalene;
2,3-dimethoxy-6-methylsulfinyl-1-i-propoxy-4-acetyloxynaphthalene;
2,3-dimethoxy-5-benzylsulfinyl-1-n-butoxy-4-acetyloxynaphthalene; and
2,3-dimethoxy-5-methoxycarbonylmethylsulfinyl-1-i-butoxy-4-acetyloxynaphthalene.

C. Similarly, using the compounds in Part B of Example 1 above, the following compounds, for example, are prepared:
6-chloro-2,3-dimethoxy-4-ethoxy-1-i-butanoyloxynaphthalene;
6-chloro-2,3-dimethoxy-4-n-propoxy-1-(2,2-dimethylpropanoyl-oxy)naphthalene;
6-chloro-2,3-dimethoxy-4-i-propoxy-1-n-octanoyloxynaphthalene;
6-chloro-2,3,4-tri-n-butoxy-1-acetyloxynaphthalene;
6-chloro-2,3-di-s-butoxy-4-i-butoxy-1-acetyloxynaphthalene;
6-chloro-2,3-di(2,2-dimethylpropoxy)-4-s-butoxy-1-acetyloxy-naphthalene;
2,3-di-n-butoxy-4-n-pentyloxy-1-n-pentoyloxynaphthalene;
6-chloro-2,3-di-n-propoxy-4-s-pentyloxy-1-propanoyloxynaphthalene;
6-chloro-2,3-di-i-propoxy-4-n-hexyloxy-1-octanoyloxynaphthalene;
6-bromo-2,3-dimethoxy-4-i-hexyloxy-1-acetyloxynaphthalene;
6-fluoro-2,3-dimethoxy-4-benzyloxy-1-acetyloxynaphthalene;
5-chloro-2,3-dimethoxy-4-(4-chlorobenzyloxy)-1-acetyloxynaphthalene;
5-cyano-2,3-dimethoxy-4-(4-methoxyphenylethoxy)-1-acetyloxynaphthalene;
6-cyano-2,3-dimethoxy-4-(2,4-dichlorophenyl-n-propoxy)-1-acetyloxynaphthalene;
6-methylamino-2,3-dimethoxy-4-(3-methylphenyl-n-butoxy)-1-acetyloxynaphthalene;
6-diethylamino-2,3-dimethoxy-4-(2-fluorophenyl-n-hexyloxy)-1-propanoyloxynaphthalene;
2,3,6-trimethoxy-4-ethoxy-1-n-pentanoyloxynaphthalene;
2,3,6-triethoxy-4-n-propoxy-1-n-hexanoyloxynaphthalene;
6-i-butoxy-2,3-dimethoxy-4-i-propoxy-1-(2,2-dimethylpropanoyloxy)naphthalene;
6-phenylethoxy-2,3-dimethoxy-4-n-butoxy-1-acetyloxynaphthalene;
6-methyl-2,3-dimethoxy-4-i-butoxy-1-acetyloxynaphthalene;
6-i-propyl-2,3-dimethoxy-4-s-butoxy-1-n-octanoyloxynaphthalene;
6-phenyl-2,3-dimethoxy-4-n-pentyloxy-1-acetyloxynaphthalene;
6-benzyl-2,3-dimethoxy-4-s-pentyloxy-1-propanoyloxynaphthalene;
5-chloro-2,3-di-n-pentyloxy-4-n-hexyloxy-1-n-butanoyloxy-naphthalene;
5-chloro-2,3-di-s-pentyloxy-4-i-hexyloxy-1-acetyloxynaphthalene;
5-chloro-2,3-di-n-hexyloxy-4-(3,5-dimethylbenzyloxy)-1-n-octanoyl-oxynaphthalene;
5-chloro-2,3-di-i-hexyloxy-4-(4-ethylphenylethoxy)-1-acetyloxynaphthalene;
5-chloro-2,3-dimethoxy-4-(2-propoxyphenyl-n-propoxy)-1-(2,2-dimethylpropanoyloxy)naphthalene;
6-chloro-2,3-dimethoxy-4-benzyloxy-1-n-butanoyloxynaphthalene;
6-chloro-2,3-diethoxy-4-(4-chlorobenzyloxy)-1-acetyloxy-naphthalene;
6-chloro-2,3-diethoxy-4-(4-methyloxyphenylethoxy)-1-n-propanoyloxynaphthalene;
6-chloro-2,3,4-triethoxy-1-(2,2-dimethylpropanoyloxy)-naphthalene;
6-chloro-2,3,4-tri-n-propoxy-1-i-butanoyloxynaphthalene;
6-chloro-2,3-di-n-propoxy-4-i-propoxy-1-(2,2-dimethylpropanoyloxy)naphthalene;
2,3,5-trimethoxy-4-n-butoxy-1-acetyloxynaphthalene;
2,3,5-trimethoxy-4-i-butoxy-1-n-propanoyloxynaphthalene;
2,3,5-trimethoxy-4-s-butoxy-1-(2,2-dimethylpropanoyloxy)naphthalene;
2,3,6-trimethoxy-4-n-pentyloxy-1-n-propanoyloxynaphthalene;
2,3,6-trimethoxy-4-s-pentyloxy-1-(2,2-dimethylpropanoyloxy)naphthalene;
6-chloro-2,3-di-n-propoxy-4-n-hexyloxy-1-acetyloxynaphthalene;
6-chloro-2,3-di-i-propoxy-4-i-hexyloxy-1-acetyloxynaphthalene;
6-chloro-2,3-di-i-propoxy-4-(2,4-dichlorophenyl-n-propoxy)-1-n-butanoyloxy-naphthalene;
6-chloro-2,3-di-i-propoxy-4-(3-methylphenyl-n-butoxy)-1-i-butanoyloxynaphthalene;
6-chloro-2,3-di-i-propoxy-4-(2-fluorophenyl-n-hexyloxy)-1-(2,2-dimethylpropanoyloxy)naphthalene;
2,3,6-trimethoxy-4-(3,5-dimethylbenzyloxy)-1-acetyloxynaphthalene;
5-methyl-2,3-dimethoxy-4-(4-ethylphenylethoxy)-1-acetyloxynaphthalene;
5-methyl-2,3-dimethoxy-4-(2-propoxyphenphenyl-n-propoxy)-1-n-propanoyloxynaphthalene;
5-methyl-2,3-dimethoxy-4-ethoxy-1-(2,2-dimethylpropanoyloxy)naphthalene;
6-methyl-2,3-dimethoxy-4-n-propoxy-1-n-propanoyloxynaphthalene;
6-methyl-2,3-dimethoxy-4-i-propoxy-1-i-butanoyloxynaphthalene;
6-methyl-2,3-dimethoxy-4-n-butoxy-1-(2,2-dimethylpropanoyloxy)naphthalene;
6,7-dimethyl-2,3-dimethoxy-4-i-butoxy-1-acetyloxynaphthalene;
6,7-dimethyl-2,3-dimethoxy-4-s-butoxy-1-n-propanoyloxynaphthalene;
6,7-dimethyl-2,3-dimethoxy-4-n-pentyloxy-1-n-butanoyloxynaphthalene;
6,7-dimethyl-2,3-dimethoxy-4-s-pentyloxy-1-i-butanoyloxynaphthalene;
6,7-dimethyl-2,3-dimethoxy-4-n-hexyloxy-1-(2,2-dimethylpropanoyloxy)naphthalene;
2,3-dimethoxy-4-i-hexyloxy-1-benzoyloxynaphthalene;
6-chloro-2,3-dimethoxy-4-benzyloxy-1-benzoyloxynaphthalene;
6-chloro-2,3-diethoxy-4-(4-chlorobenzyloxy)-1-(2-chlorobenzoyloxy)naphthalene;
6-chloro-2,3-diethoxy-4-(4-methoxyphenylethoxy)-B 1-(3-bromobenzoyloxy)naphthalene;
6-chloro-2,3-di-n-propoxy-4-(2,4-dichlorophenyl-n-propoxy)-1-(4-ethylbenzoyl-oxy)naphthalene;
6-chloro-2,3-di-n-propoxy-4-(3-methylphenyl-n-butoxy)-1-(4-fluorobenzoyloxy)naphthalene;

6-chloro-2,3-diethoxy-4-(2-fluorophenyl-n-hexyloxy)-1-(2-methoxybenzoyloxy)naphthalene;
6-chloro-2,3-di-n-butoxy-4-ethoxy-1-(2-hydroxy-4-chlorobenzoyloxy)naphthalene;
6-chloro-2,3-di-n-butoxy-4-n-propoxy-1-(3,5-dichlorobenzoyloxy)naphthalene;
6-chloro-2,3-dimethoxy-4-i-propoxy-1-(2,6-dimethylbenzoyloxy)naphthalene;
2,3-dimethoxy-4-n-butoxy-1-phenylacetyloxynaphthalene;
6-chloro-2,3-dimethoxy-4-i-butoxy-1-phenylacetyloxynaphthalene;
6-chloro-2,3-diethoxy-4-s-butoxy-1-(2-chlorophenylacetyloxynaphthalene;
6-chloro-2,3-diethoxy-4-n-pentyloxy-1-(4-fluorophenylacetyloxynaphthalene;
6-chloro-2,3-di-n-propoxy-4-s-pentyloxy-1-(2-methoxyphenylacetyloxy)naphthalene;
6-chloro-2,3-di-n-propoxy-4-n-hexyloxy-1-(4-methoxyphenylacetyloxy)naphthalene;
6-chloro-2,3-di-n-propoxy-4-i-hexyloxy-1-(4-ethoxyphenylacetyloxy)naphthalene;
6-chloro-2,3-dimethoxy-4-(3,5-dimethylbenzyloxy)1-(2-methylphenyl-acetyloxy)naphthalene;
6-chloro-2,3-dimethoxy-4-(4-ethylphenylethoxy)-1-(4-ethylphenylacetyloxy)naphthalene;
2,3-diphenoxy-4-(2-propoxyphenyl-n-propoxy)-1-acetyloxynaphthalene;
6-chloro-2,3-dipbenoxy-4-benzyloxy-1-acetyloxynaphthalene;
6-chloro-2,3-di(2-chlorophenoxy)-4-(4-chlorobenzyloxy)-1-benzoyloxynaphthalene;
6-chloro-2,3-di(2-chlorophenoxy)-4-(4-methoxyphenylethoxy)-1-(4-benzoyloxy)naphthalene;
6-chloro-2,3-diphenoxy-4-ethoxy-1-n-butanoyloxynaphthalene;
6-chloro-2,3-di(4-chlorophenoxy)-4-n-propoxy-1-4-benzoyloxynaphthalene;
6-chloro-2,3-di(4-methoxyphenoxy)-4-i-propoxy-1-phenylacetyloxynaphthalene;
6-chloro-2,3-di(2-hydroxy-4-chlorophenoxy)-4-n-butoxy-1-phenylacetyloxynaphthalene;
6-chloro-2,3-di(3-methylphenoxy)-4-i-butoxy-1-acetyloxynaphthalene;
6-chloro-2,3-di(4-ethylphenoxy)-4-s-butoxy-1-benzyloxy-naphthalene;
6-chloro-2,3-di(2-fluorophenoxy)-4-n-pentyloxy-1-(2-methylbenzoyloxy)naphthalene;
2,3-dimethoxy-5-(imidazol-2-ylsulfinyl)-4-n-pentyloxy-1-acetyloxynaphthalene;
2,3-dimethoxy-6-(2-chlorophenylsulfinyl)-4-s-pentyloxy-1-acetyloxynaphthalene;
2,3-dimethoxy-5-(3-chlorophenylsulfinyl)-4-n-hexyloxy-1-acetyloxynaphthalene;
2,3-dimethoxy-6-(4-chlorophenylsulfinyl)-4-i-hexyloxy-1-acetyloxynaphthalene;
2,3-dimethoxy-5-(2,6-dichlorophenylsulfinyl)-4-benzyloxy-1-acetyloxynaphthalene;
2,3-dimethoxy-5-(4-fluorophenylsulfinyl)-4-(4-chlorobenzyloxy)-1-acetyloxynaphthalene;
2,3-dimethoxy-5-(2-bromophenylsulfinyl)-4-(4-methoxyphenylethoxy)-1-acetyloxynaphthalene;
2,3-dimethoxy-5-(4-bromophenylsulfinyl)-4-(2,4-dichlorophenyl-n-propoxy)-1-acetyloxynaphthalene;
2,3-diethoxy-6-(4-methoxyphenylsulfinyl)-4-(3-methylphenyl-n-butoxy)-1-acetyloxynaphthalene;
2,3-dipropoxy-6-(4-nitrophenylsulfinyl)-4-(2-fluorophenyl-n-hexyloxy)-1-acetyloxynaphthalene;

2,3-dimethoxy-6-(pyrimidin-2-ylsulfinyl)-4-ethoxy-1-acetyloxynaphthalene;
2,3-dimethoxy-5-(pyrimidin-2-ylsulfinyl)-4-n-propoxy-1-acetyloxynaphthalene;
2,3-dimethoxy-6-methylsulfinyl-4i-propoxy-1-acetyloxynaphthalene;
2,3-dimethoxy-5-benzylsulfinyl-4-n-butoxy-1-acetyloxynaphthalene; and
2,3-dimethoxy-5-methoxycarbonylmethylsulfinyl-4-i-butoxy-1-acetyloxynaphthalene.

EXAMPLE 4

(Preparation of a compound of formula (Ic))

A. A solution of 6-chloro-2,3-dimethoxy-1-hydroxy-4-acetoxy-naphthalene and 6-chloro-2,3-dimethoxy-4-hydroxy-1-acetyloxy-naphthalene (1.0 g) in ether (100 ml) was treated with a solution of excess diazomethane in ether, generated from Diazald ® (Aldrich). The solution was evaporated to yield an isomeric mixture of 6-chloro-2,3,4-trimethoxy-1-acetyloxynaphthalene and 6-chloro-1,2,3-trimethoxy-4-acetyloxynaphthalene (0.84 g) as an oil after flash chromatography over silica gel.

B. Similarly, proceeding as above in Part A and using the appropriate compound from Example 1 the following compounds, for example, are prepared:
6-chloro-1,2,3-trimethoxy-4n-propanoyloxynaphthalene;
6-ethylmethylamino-1,2,3-trimethoxy-4-n-butanoyloxynaphthalene;
1,2,3-trimethoxy-4-(2,2-dimethylpropanoyloxy)naphthalene, oil;
5-methyl-1,2,3-trimethoxy-4-i-butanoyloxynaphthalene;
6-chloro-2,3-diethoxy-1-methoxy-4-(4-ethoxybenzoyloxy)naphthalene;
6-chloro-2,3-diphenoxy-1-methoxy-4-n-butanoyloxynaphthalene;
2,3-di-n-butoxy-6-(2-ethylphenylsulfinyl)-1-methoxy-4-acetyloxynaphthalene;
6-chloro-2,3,4-trimethoxy-1-n-propanoyloxynaphthalene;
6-ethylmethylamino-2,3,4-trimethoxy-1-n-butanoyloxynaphthalene;
6-chloro-2,3-diethoxy-4-methoxy-1-i-butanoyloxynaphthalene;
5-methyl-2,3,4-trimethoxy-1-i-butanoyloxynaphthalene;
6-chloro-2,3-diethoxy-4-methoxy-1-(4-ethoxybenzoyloxy)naphthalene;
6-chloro-2,3-diphenoxy-4-methoxy-1-n-propanoyloxynaphthalene;
2,3-di-n-butoxy-6-(2-ethylphenylsulfinyl)-4-methoxy-1-acetyloxynaphthalene;
1,2,3-trimethoxy-4-acetyloxynaphthalene;
2,3-dimethoxy-1-ethoxy-4-acetyloxynaphthalene;
2,3-diethoxy-1-methoxy-4-acetyloxynaphthalene;
1,2,3-triethoxy-4-(2,2-dimethylpropanoyloxy)naphthalene;
2,3-dimethoxy-1-n-propoxy-4-acetyloxynaphthalene;
2,3,4-trimethoxy-1-acetyloxynaphthalene;
2,3-dimethoxy-4-ethoxy-1-acetyloxynaphthalene;
2,3-diethoxy-4-methoxy-1-acetyloxynaphthalene; and
2,3,4-triethoxy-1-(2,2-dimethylpropanoyloxy)naphthalene.

C. Similarly, proceeding as in Part A above the following compounds, for example, are prepared:
6-chloro-1,2,3-trimethoxy-4-(2,2-dimethylpropanoyloxy)naphthalene, and its regioisomer, oil.

What is claimed is:

1. A compound of the formula

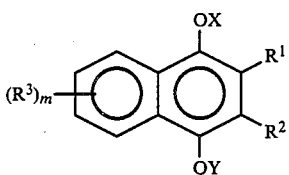

wherein:
R¹ and R² are the same and are lower alkoxy of one to six carbon atoms or phenoxy optionally substituted by one or two lower alkyl of one to four carbon atoms, lower alkoxy of one to four carbon atoms or halo;
R³ is lower alkyl of one to six carbon atoms, lower alkoxy of one to six carbon atoms, or halo and m is 0, 1 or 2 or R³ is phenyl optionally substituted by one or more substituents selected from the group consisting of lower alkyl, lower alkoxy, halo, lower acyl, lower acyloxy, cyano, nitro, amino, and lower acylamino, phenyl-lower-alkyl wherein the phenyl is optionally substituted by one or more substituents selected from the group consisting of lower alkyl, lower alkoxy, halo, lower acyl, lower acyloxy, cyano, nitro, amino, and lower acylamino, phenyl-lower-alkoxy wherein the phenyl is optionally substituted by one or more substituents selected from the group consisting of lower alkyl, lower alkoxy, halo, lower acyl, lower acyloxy, cyano, nitro, amino, and lower acylamino, amino, lower alkylamino, lower dialkylamino, halo, cyano, or $S(O)_nR$ wherein R is lower alkyl of one to six carbon atoms; phenyl optionally substituted by one or more substituents selected from the group consisting of lower alkyl, lower alkoxy, halo, lower acyl, lower acyloxy, cyano, nitro, amino, and lower acylamino; phenyl-lower-alkyl wherein the phenyl is optionally substituted by one or more substituents selected from the group consisting of lower alkyl, lower alkoxy, halo, lower acyl, lower acyloxy, cyano, nitro, amino, and lower acylamino; or heterocyclic aryl selected from the group consisting of thiapyranyl, benzothiapyranyl, furyl, pyrrolyl, imidazolyl, pyrazolyl, pyridinyl, pyrimidinyl, indolyl, quinolinyl, and imidazolyl wherein the heterocyclic aryl is optionally substituted by one or more substituents selected from the group consisting of lower alkyl, lower alkoxy, halo and cyano and the pharmaceutically acceptable acid addition salts thereof; and m is 1 and n is 0, 1 or 2; and
one of X or Y is C(O)W and the other X or Y is hydrogen wherein
W is alkyl of one to seven carbon atoms, phenyl or benzyl optionally substituted with one or two lower alkyl of one to four carbon atoms, lower alkoxy of one to four carbon atoms or halo.

2. The compound of claim 1 in combination with its regioisomer.

3. The compound of claim 1 wherein m is 1.

4. The compound of claim 3 wherein R³ is lower alkyl of one to six carbon atoms, lower alkoxy of one to six carbon atoms or halo.

5. The compound of claim 4 wherein either X or Y is acetyl, the other X or Y is hydrogen, R¹ and R² are both methoxy, and R³ is chloro.

6. The compound of claim 5 wherein X is hydrogen, Y is acetyl, R¹ and R² are both methoxy and R³ is chloro which is 6-chloro-2,3-dimethoxy-1-hydroxy-4-acetyloxynaphthalene.

7. The compound of claim 6 in combination with its regioisomer.

8. The compound of claim 7 wherein X is acetyl, Y is hydrogen, R¹ and R² are both methoxy and R³ is chloro which is 6-chloro-2,3-dimethoxy-4-hydroxy-1-acetyloxynaphthalene.

9. The compound of claim 4 wherein X is hydrogen, Y is 2,2-dimethylpropanoyl, R¹ and R² are both methoxy and R³ is chloro which is 6-chloro-2,3-dimethoxy-1-hydroxy-4-(2,2-dimethylpropanoyloxy)naphthalene.

10. The compound of claim 9 in combination with its regioisomer.

11. The compound of claim 4 wherein X is 2,2-dimethylpropanoyl, Y is hydrogen, R¹ and R² are both methoxy and R³ is chloro which is 6-chloro-2,3-dimethoxy-4-hydroxy-1-(2,2-dimethylpropanoyloxy)naphthalene.

12. The compound of claim 1 wherein m is 0.

13. The compound of claim 1 wherein X is hydrogen, Y is acetyl and R¹ and R² are both methoxy which is 2,3-dimethoxy-1-hydroxy-4-acetyloxynaphthalene.

14. The compound of claim 1 wherein X is hydrogen, Y is 2,2-dimethylpropanoyl and R¹ and R² are both methoxy which is 2,3-dimethoxy-1-hydroxy-4-(2,2-dimethylpropanoyloxy)naphthalene.

15. The compound of claim 1 wherein m is 2.

16. A compound of claim 15. wherein each R³ is the same and is lower alkyl of one to six carbon atoms, lower alkoxy of one to six carbon atoms or halo.

17. A composition in a form suitable for topical administration for treating the condition of psoriasis which composition comprises a pharmaceutically acceptable carrier and a psoriasis relieving amount of a compound of claim 1.

18. A method of treating psoriasis in mammals which comprises applying an effective amount of a compound of claim 1.

* * * * *